(12) United States Patent
Garcon et al.

(10) Patent No.: US 6,372,227 B1
(45) Date of Patent: Apr. 16, 2002

(54) VACCINES

(75) Inventors: Nathalie Garcon, Wavre; Patricia Marie Christine Aline Francoise Momin, Brussells, both of (BE)

(73) Assignee: SmithKline Beecham Biologicals, s.a., Rixensart (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/486,996

(22) PCT Filed: Sep. 2, 1998

(86) PCT No.: PCT/EP98/05714

§ 371 Date: Apr. 24, 2000

§ 102(e) Date: Apr. 24, 2000

(87) PCT Pub. No.: WO99/12565

PCT Pub. Date: Mar. 18, 1999

(30) Foreign Application Priority Data

Sep. 5, 1997 (GB) ............................................. 9718901

(51) Int. Cl.[7] .......................... A61K 45/00; A61K 47/44
(52) U.S. Cl. ................................ 424/283.1; 424/184.1; 424/278.1; 424/283.1; 514/937; 514/938; 514/943
(58) Field of Search ............................. 424/455, 184.1, 424/278.1, 283.1; 514/937, 938, 943

(56) References Cited

U.S. PATENT DOCUMENTS

| 4,806,350 A | * | 2/1989 | Gerber | ........................... 424/88 |
| 5,585,103 A | | 12/1996 | Raychaudhuri et al. | .. 424/278.1 |
| 6,270,769 B1 | | 8/2001 | Raychaudhuri et al. | .. 424/184.1 |

FOREIGN PATENT DOCUMENTS

| WO | WO 90/03184 | 4/1990 |
| WO | WO 95/17210 | 6/1995 |
| WO | WO 96/33739 | 10/1996 |
| WO | WO 97/01640 | 1/1997 |
| WO | WO 98/15287 | 4/1998 |

OTHER PUBLICATIONS

Paul *Fundamental Immunology*, (Philadelphia & New York, Lippincott–Raven Publishers, 1993), p. 1310 QR181.F84.*

Cruse et al. *Illustrated Dictionary of Immunology* (Boca Raton, FL, CRC Press, Inc., 1995), p. 309.*

* cited by examiner

*Primary Examiner*—Jeffrey Stucker
(74) *Attorney, Agent, or Firm*—Zoltan Kerekes; Stephen Venetianer; Charles M. Kinzig

(57) ABSTRACT

The present invention relates to oil in water emulsion compositions, their use in medicine, in particular to their use in augmenting immune responses to a wide range of antigens, and to methods of their manufacture; the compositions having oil phase and an aqueous phase, a sterol and a saponin; the sterol being present in the oil phase and the saponin being present in the aqueous phase.

25 Claims, 12 Drawing Sheets s# VACCINES

CROSS REFERENCE TO RELATED APPLICATIONS

This application is a 371 of PCT/EP98/05714, filed Sep. 2, 1998, which claims priority from GB 9718901.3, filed Sep. 5, 1997.

STATEMENT REGARDING FEDERALLY SPONSORED RESEARCH OR DEVELOPMENT

Not Applicable.

REFERENCE TO MICROFICHE APPENDIX

Not Applicable.

BACKGROUND OF THE INVENTION

Induction of cytotoxic lymphocyte (CTL) responses occurs naturally during infection of a target cell, or uncontrolled synthesis of a tumor antigen, wherein enzymatic degradation of the target antigen takes place in the cell cytoplasm. This phenomenon allows cytoplasmic peptides derived from the pathogen, or tumor specific antigen, to enter the Th1 (endogenous antigen processing) pathway and be presented on the surface of the cell associated with an MHC class 1 molecule. If a vaccine antigen does not enter into the cytoplasm of the host cell, then it might be taken up by the cell and enter the exogenous antigen processing pathway and ultimately be presented on the surface of the cell associated with a MHC class II molecule. This alternative route generally results in T-helper responses and antigen specific antibody responses.

After conventional vaccination with subunit or non-living vaccines, an antigen generally does not enter the cytoplasm of a host cell, and therefore will not enter the endogenous antigen processing pathway and ultimately will not induce a CTL response. CTL induction is believed to correlate with Th-1 cytokine profile responses, specifically with IFN-γ and IL-2 secretion. IFN-γ secretion is associated with protective responses against intracellular pathogens, including parasites, bacteria and viruses. Activation of leucocytes by IFN-γ enhances killing of intracellular pathogens and increases expression of Fc receptors. Direct cytotoxicity may also occur, especially in synergy with lymphotoxin (another product of TH1 cells). IFN-γ is also both an inducer and a product of NK cells, which are major innate effectors of protection. TH1 type responses, either through IFN-γ or other mechanisms, provide preferential help for murine IgG2a, and human IgG1, immunoglobulin isotypes.

International patent application No. WO 95/17210 discloses an adjuvant emulsion system based on squalene, α-tocopherol, and polyoxyethylene sorbitan monooleate (TWEEN 80), optionally formulated with the immunostimulants QS21 and/or 3D-MPL. This adjuvant formulation is a very potent inducer of a wide range of immune responses.

These oil in water emulsions, when formulated with 3 De-O-acylated monophosphoryl lipid A (3D-MPL) and QS21 are potent inducers of Th1 type immune responses. Accordingly, this system when associated with antigen preferentially stimulate the sub-isotype of IgG associated with Th1 responses (for example, murine IgG2a and human IgG1) and also will induce significant levels of IFN-γ production and antigen specific CTL responses. The observation that the basic oil in water/QS21/3D-MPL formulation can induce strong CTL responses is significant, as these responses in certain animal models have been shown to induce protection against disease.

Immunologically active saponin fractions (e.g. Quil A) having adjuvant activity derived from the bark of the South American tree Quillaja Saponaria Molina are known in the art. Derivatives of Quil A, for example QS21 (an HPLC purified fraction derivative of Quil A), and the method of its production is disclosed in U.S. Pat. No. 5,057,540. Amongst QS21 (known as QA21) other fractions such as QA 17 are also disclosed. The use of such saponins in isolation is accompanied with disadvantage in that local necrosis, that is to say, localized tissue death, occurs at the injection site, thereby leading to pain.

3 De-O-acylated monophosphoryl lipid A is a well known adjuvant manufactured by Ribi Immunochem, Montana. Chemically it is often supplied as a mixture of 3 De-O-acylated monophosphoryl lipid A with either 4, 5, or 6 acylated chains. It can be prepared by the methods taught in GB 2122204B. A preferred form of 3 De-O-acylated monophosphoryl lipid A is in the form of an emulsion having a small particle size less than 0.2 μcm in diameter, and its method of manufacture is disclosed in European Patent No. EP 0 671 948 B1.

In order for any oil in water composition to be suitable for human administration, the oil phase of the emulsion system has to comprise a metabolizable oil. The meaning of the term metabolizable oil is well known in the art. Metabolizable can be defined as "being capable of being transformed by metabolism" (Dorland's Illustrated Medical Dictionary, W. B. Sanders Company, 25th edition (1974)). The oil may be any vegetable oil, fish oil, animal oil or synthetic oil, which is not toxic to the recipient and is capable of being transformed by metabolism. Nuts, seeds, and grains are common sources of vegetable oils. Synthetic oils are also part of this invention and can include commercially available oils such as NEOBEE® and others. Squalene (2,6,10,15,19,23-Hexamethyl-2,6,10,14,18,22-tetracosahexaene) is an unsaturated oil which is found in large quantities in shark-liver oil, and in lower quantities in olive oil, wheat germ oil, rice bran oil, and yeast, and is a particularly preferred oil for use in this invention. Squalene is a metabolizable oil virtue of the fact that it is an intermediate in the biosynthesis of cholesterol (Merck index, 10th Edition, entry no. 8619).

Oil in water emulsions per se are well known in the art, and have been suggested to be usefull as adjuvant compositions (EPO 399843).

The oil in water emulsions described in International patent application No. WO 95/17210 obviously hold great advantages over conventional non-Th1 inducing adjuvants. However, the inclusion of QS21 has so far made this potent adjuvant reactogenic, leading to pain at the site of injection.

Formulations comprising QS21 with a sterol are known from International Patent Application No. PCT/EP96/01464. No oil in water emulsions are disclosed in this document. Sterols are well known in the art, for example cholesterol is well known and is, for example, disclosed in the Merck Index, 11th Edn., page 341, as a naturally occurring sterol found in animal fat.

BRIEF SUMMARY OF THE INVENTION

The present invention relates to an oil in water emulsion compositions, their use in medicine, in particular to their use in augmenting immune responses to a wide range of antigens, and to methods of their manufacture; the oil in water emulsion comprising a metabolizable oil, a saponin and a sterol.

derived from the experimental groups after stimulation with TRAP and RTS,S antigens.

Figure 2:
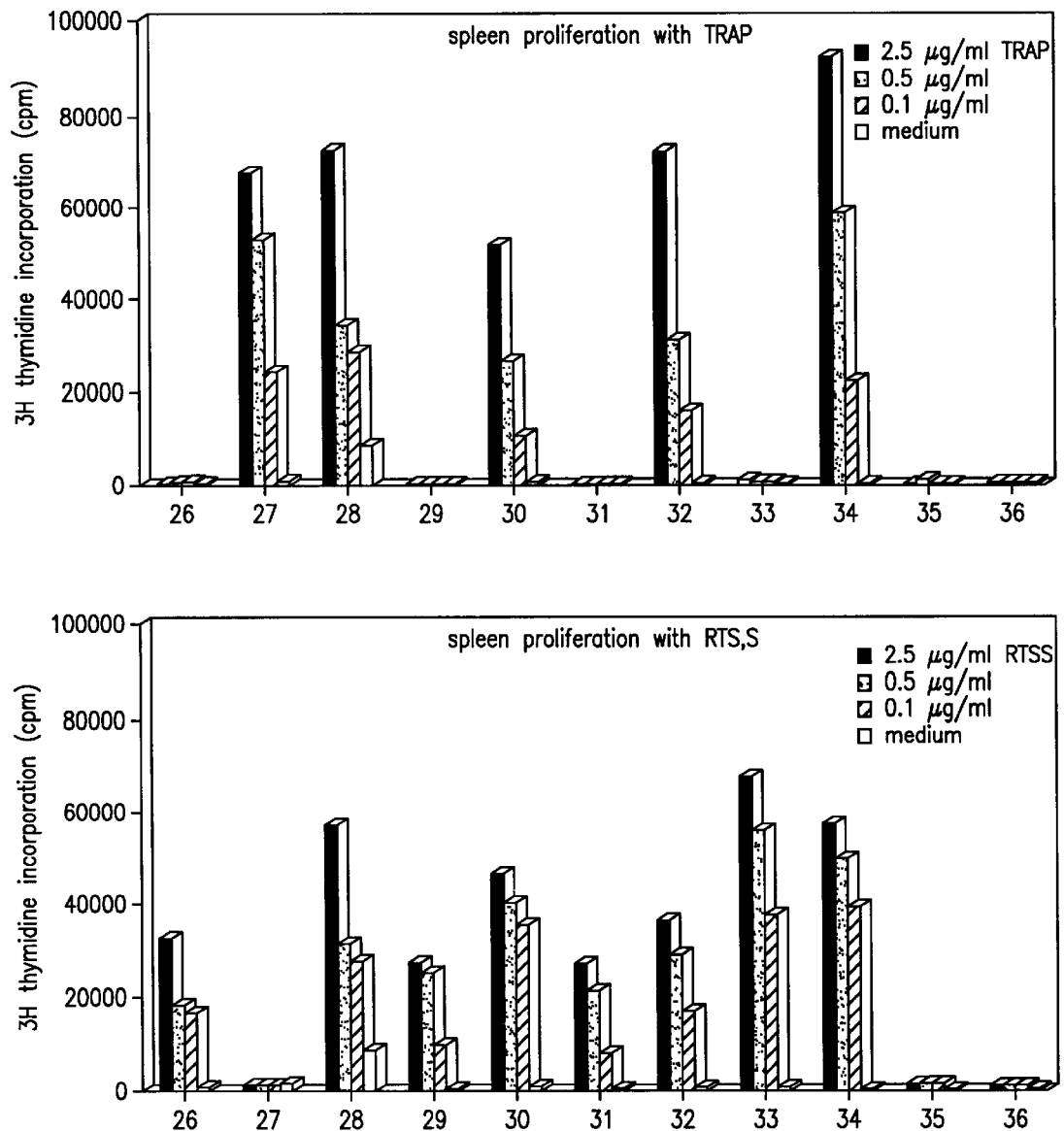

FIG. 2 shows the proliferative responses of splenic cells (in raw counts per minute (CPM) form) derived from the experimental groups after stimulation with TRAP and RTS,S antigens.

Figure 3:
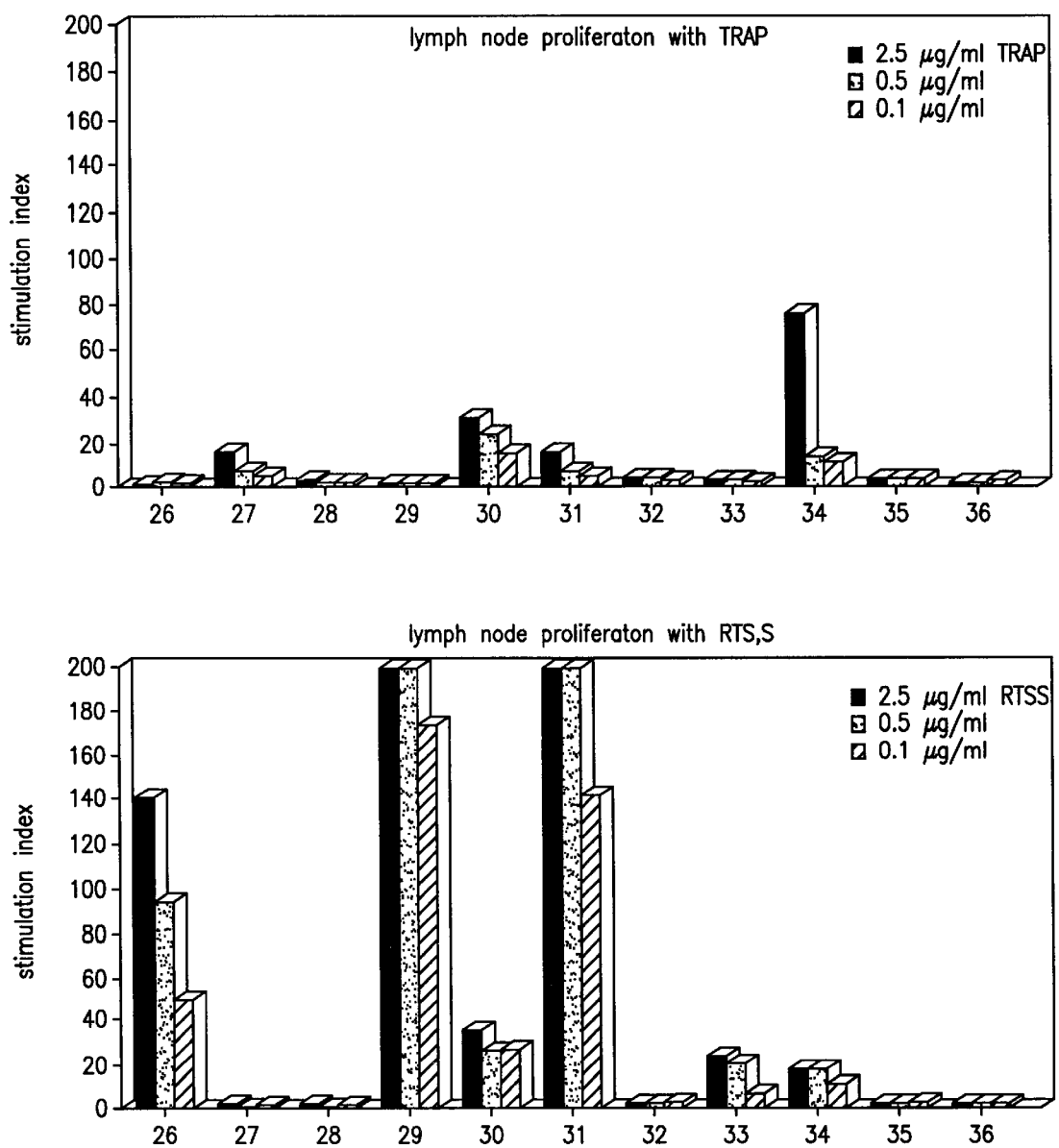

FIG. 3 shows the proliferative responses of popliteal lymph node cells (Stimulation index) derived from the experimental groups after stimulation with TRAP and RTS,S antigens.

Figure 4:
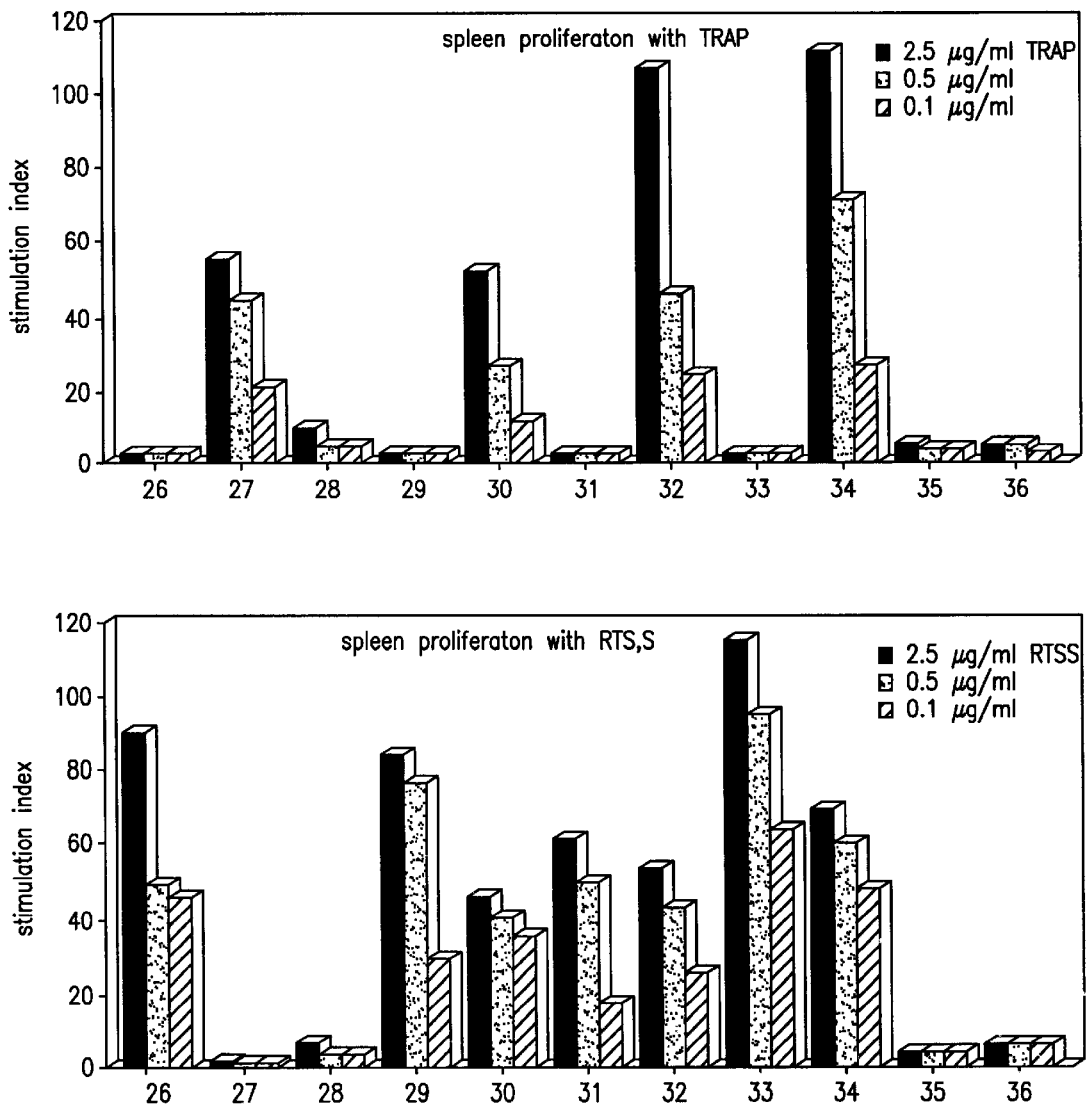

FIG. 4 shows the proliferative responses of splenic cells (Stimulation index) derived from the experimental groups after stimulation with TRAP and RTS,S antigens.

Figure 5:
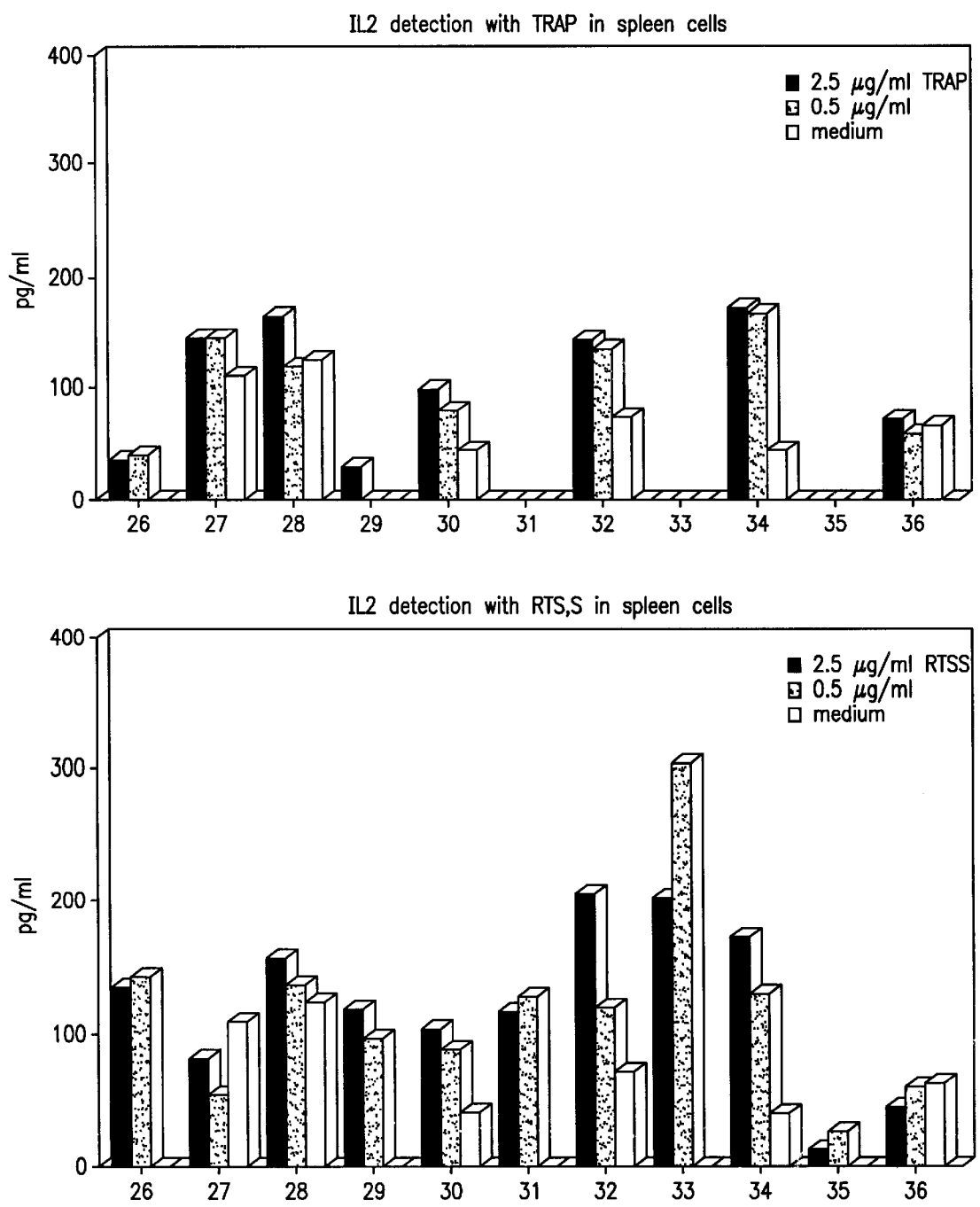

FIG. 5 shows the IL-2 production of spleen cells after stimulation with TRAP or RTS,S antigen 14 days after VII.

Figure 6:
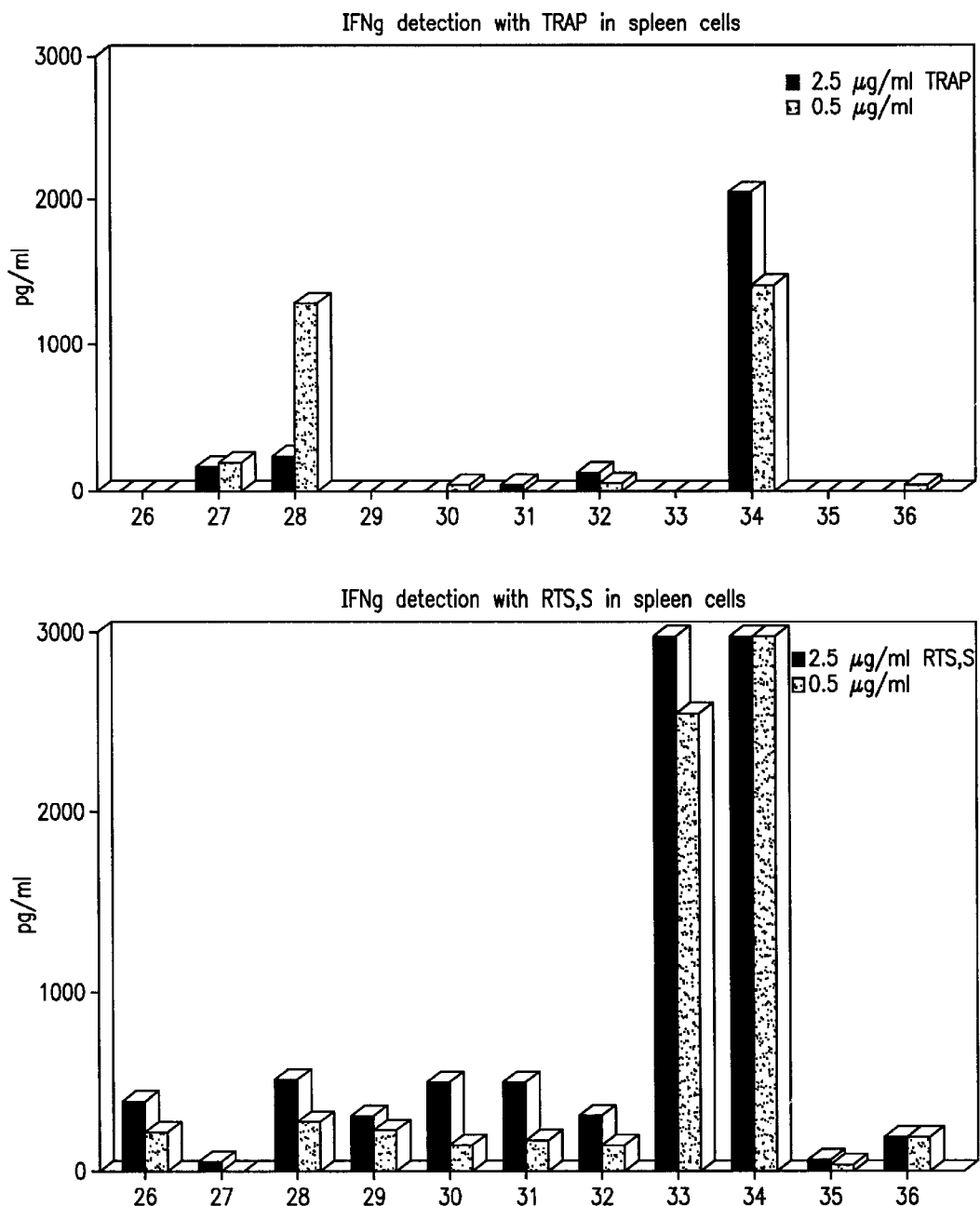

FIG. 6 shows the IFN-γ production by spleen cells after stimulation with TRAP or RTS,S antigen 14 days after VII.

Figure 7:
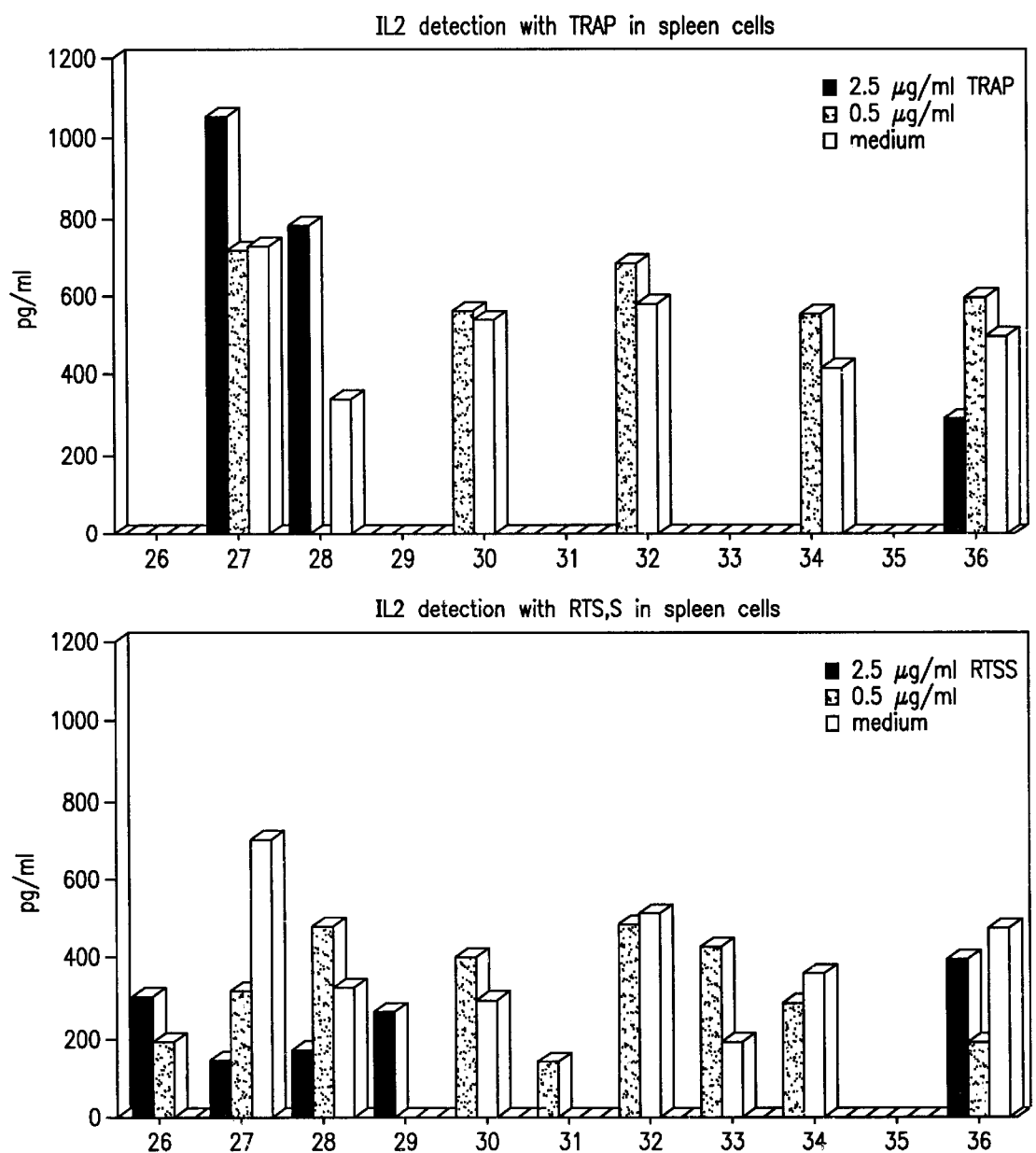

FIG. 7 shows the IL-5 production by spleen cells after stimulation with TRAP or RTS,S antigen 14 days after VII.

Figure 8:
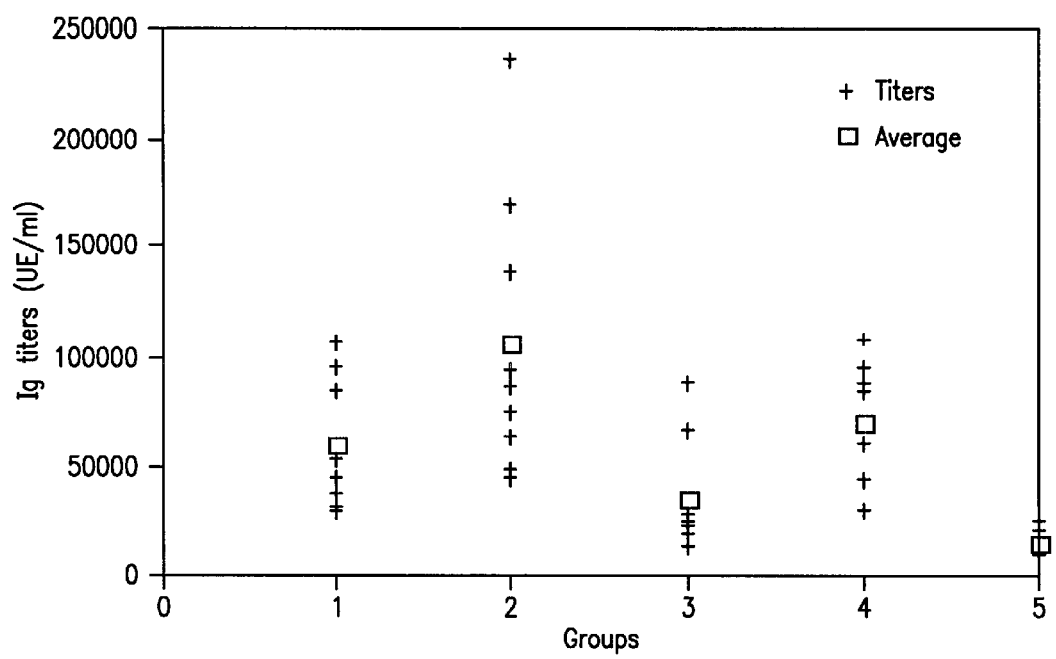

FIG. 8 shows the titres of anti-Hepatitis B virus antibody responses (Ig) expressed as both individual mouse sera and average (21 days post II).

Figure 9:
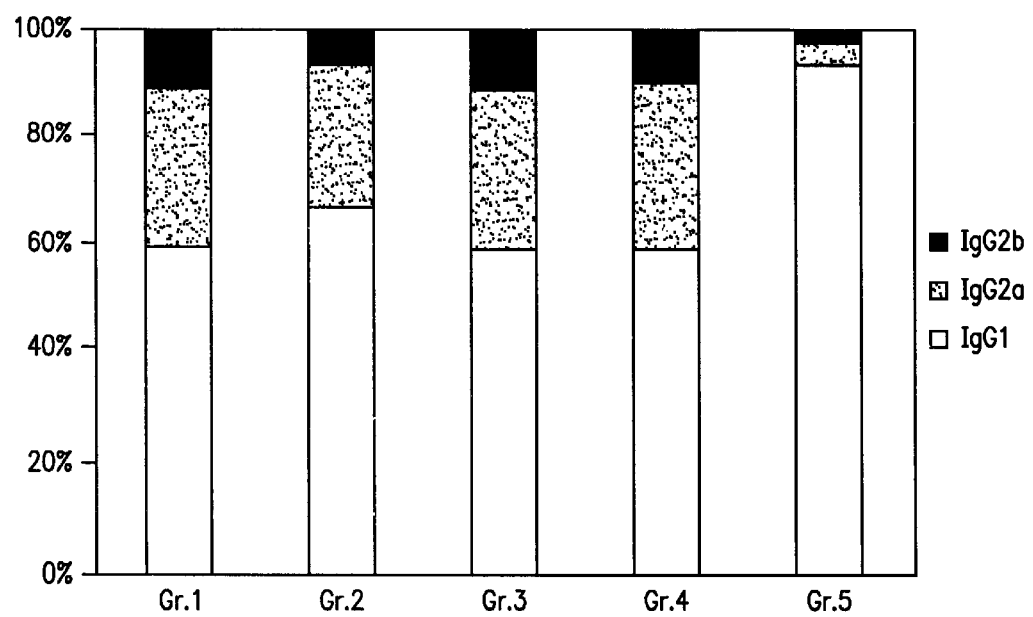

FIG. 9 shows the sub-isotype distribution of Hbs specific IgG in the serum the vaccinated mice.

Figure 10:
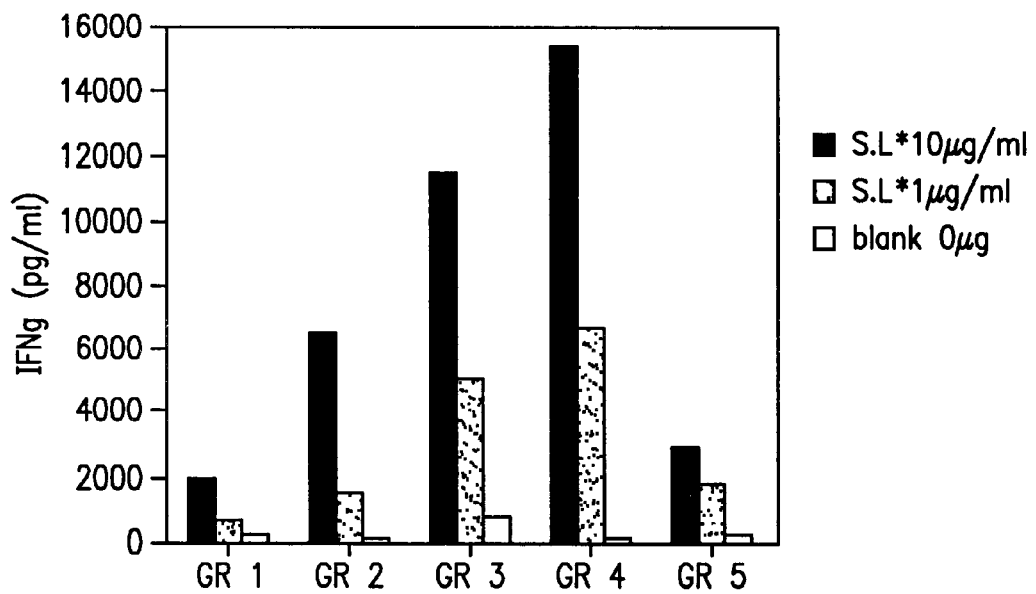

FIG. 10 shows the results of analysis of IFN-γ production by splenic cells (mean of data obtained with three pools/group).

Figure 11:
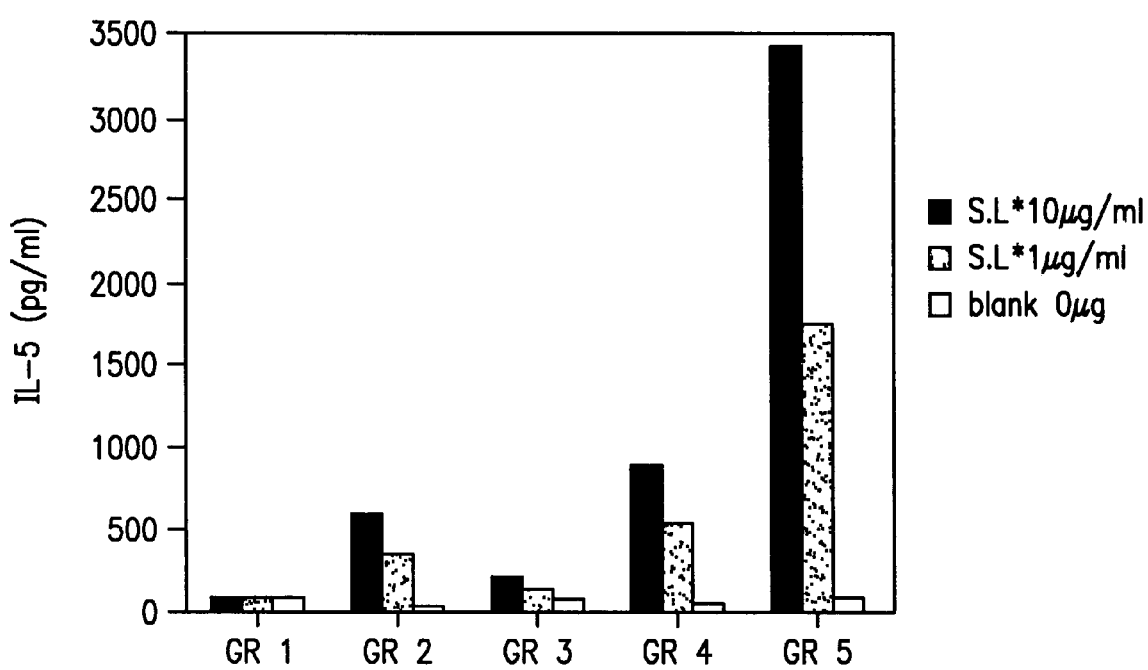

FIG. 11 shows the results of analysis of IL-5 production by splenic cells (mean of data obtained with three pools/group).

Figure 12:
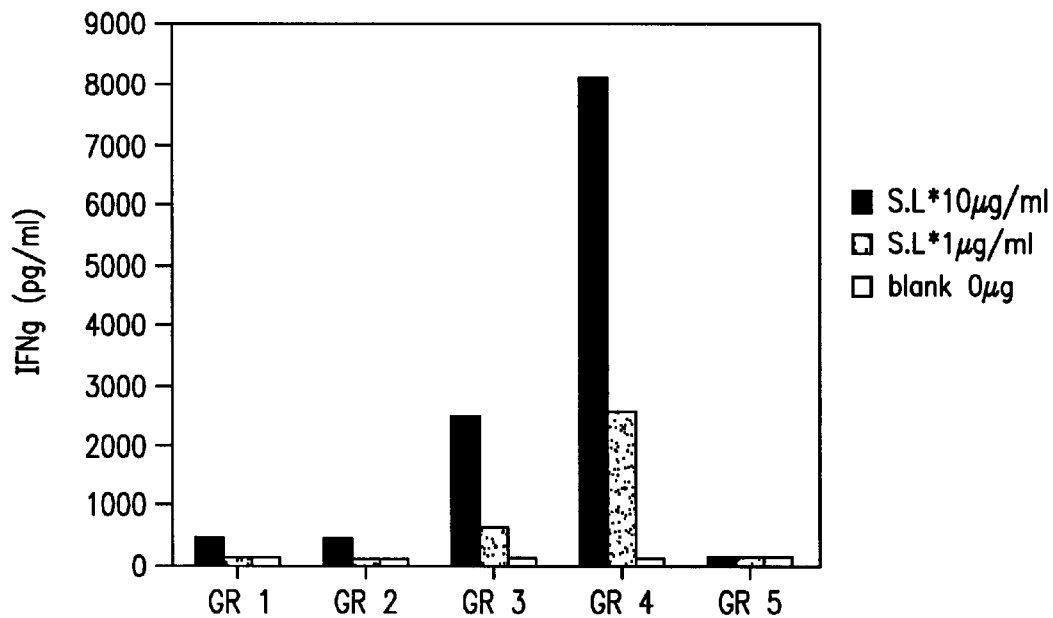

FIG. 12 shows the results of analysis of IFN-γ production by Iliac lymph node cells (mean of data obtained with three pools/group).

Figure 13:
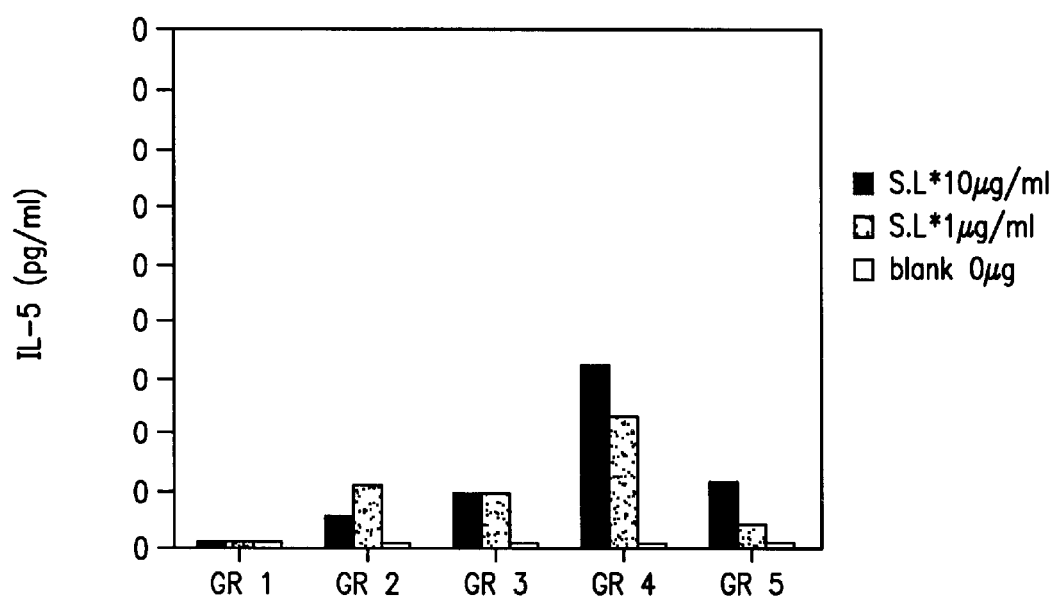

FIG. 13 shows the results of analysis of IL-5 production by Iliac lymph node cells (mean of data obtained with three pools/group).

Figure 14:
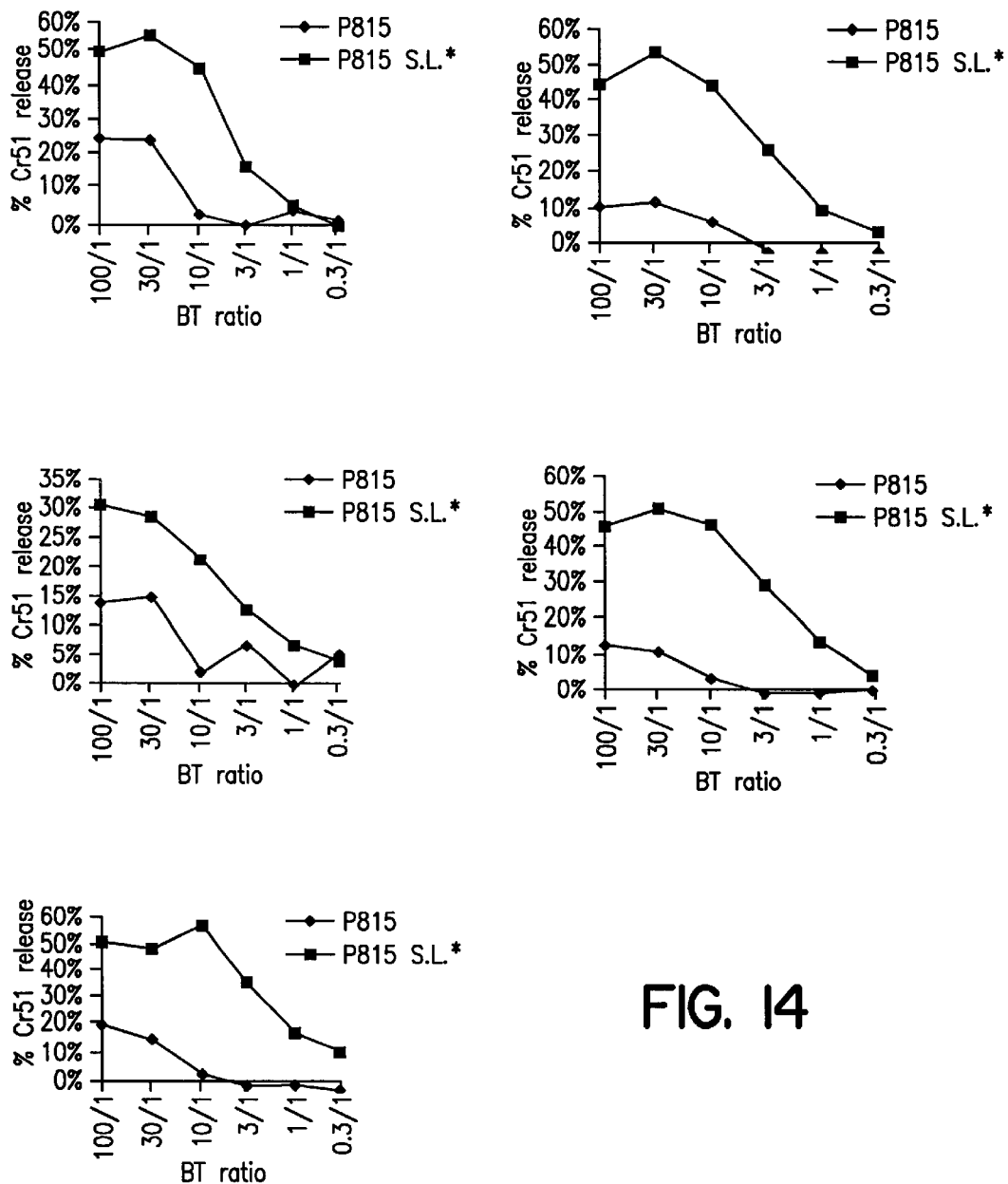

FIG. 14 shows the CTL activity of splenic T-cells stimulated in vitro for 7 days with S,L* antigen (mean % specific lysis of three pools).

Figure 15:
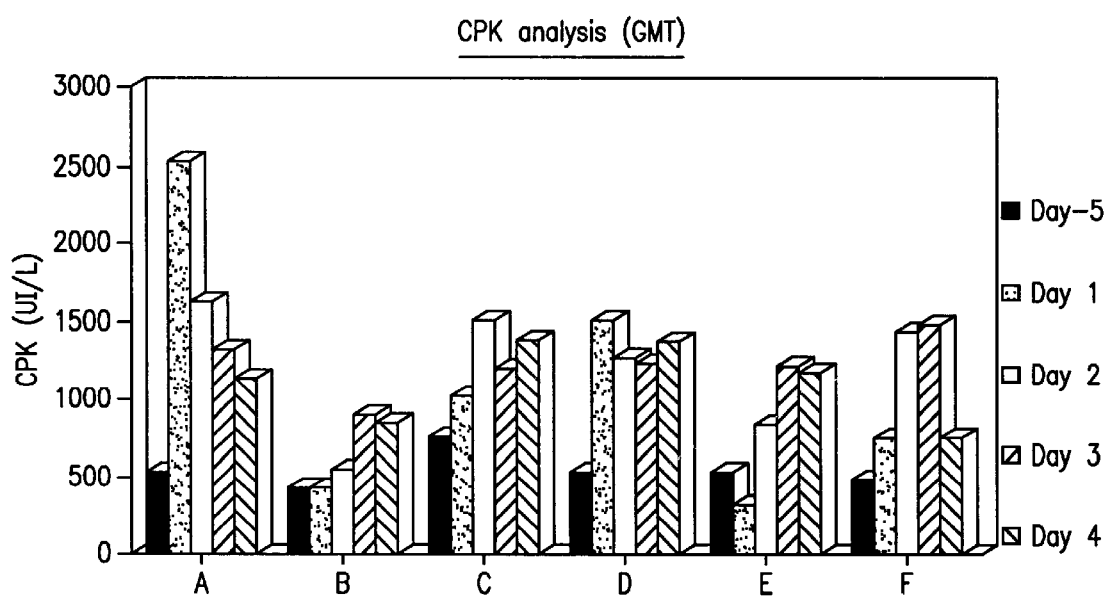

FIG. 15 is a summary figure showing the mean CPK results for each group.

DETAILED DESCRIPTION OF THE INVENTION

The present inventors have found that oil in water formulations containing a sterol, and QS21, have reduced local reactogenicity after injection into a host with respect to comparable emulsions formulated without a sterol. This is surprising since sterols, being oil soluble, would be expected to dissolve into the heart of the oil droplet, whilst on the other hand QS21 is primarily expected to be associated with the aqueous phase. Therefore, it would be expected that the sterol would be physically distinct from the QS21. Nonetheless, these formulations are surprisingly less reactogenic than those oil in water emulsions not containing a sterol.

Accordingly, one preferred embodiment of the present invention provides a composition comprising a saponin, an oil in water emulsion, and a sterol. Especially preferred embodiments of this include compositions wherein the saponin is the non-toxic fraction of Quil A known as QS21, the oil in water emulsion comprises a metabolisible oil, such as squalene, and wherein the sterol is cholesterol. Such a composition may further comprise other immunomodulators including: α-tocopherol and polyoxyethylene sorbitan monooleate (TWEEN 80), and 3D-MPL. The inclusion of cholesterol in the formulation much reduces the local reactogenicity of the composition once injected into a recipient. Other sterols that can easily act as alternatives for cholesterol include β-sitosterol, stigmasterol, ergosterol, and ergocalciferol.

Such embodiments of the present invention are used as vaccine adjuvant systems, and once combined with antigen form potent vaccines. Advantageously they preferentially induce a Th1 response.

Embodiments of the present invention include composition comprising an oil in water emulsion, a saponin and a sterol, characterised in that a reduced reatogenicity profile is induced upon administration to a host in comparison to the reactogenicity profile observed after administration of the same composition from which the sterol has been omitted.

Previous examples of oil in water adjuvant emulsions as disclosed in International patent application No. WO 95/17210 involved large quantities of squalene. The ratio of squalene:saponin (w/w) in such vaccine preparations was in the region of 240:1. An additional benefit that the addition of cholesterol bestows is the opportunity to reduce the total level of oil in the emulsion. This leads to a reduced cost of manufacture, improvement of the overall comfort of the vaccination, and also qualitative and quantitative improvements of the resultant immune responses, such as improved IFN-γ production. Accordingly, the adjuvant system of the present invention typically comprises a ratio of squalene-:saponin (w/w) in the range of 200:1 to 300:1, also the present invention can be used in a "low oil" form the preferred range of which is 1:1 to 200:1, preferably 20:1 to 100:1, and most preferably substantially 48:1, this vaccine retains the beneficial adjuvant properties of all of the components, with a much reduced reactogenicity profile. Accordingly, the particularly preferred embodiments have a ratio of squalene:QS21 (w/w) in the range of 1:1 to 250:1, also a preferred range is 20:1 to 200:1, preferably 20:1 to 100:1, and most preferably substantially 48:1.

The emulsion systems of the present invention have a small oil droplet size in the sub-micron range. Preferably the oil droplet sizes will be in the range 120 to 750 nm, and most preferably from 120–600 nm in diameter.

The formulations of the invention are suitable for a broad range of monovalent or polyvalent vaccines, once combined with an antigen or antigenic composition/combination. Additionally the oil in water emulsion may contain 3 de-O-acylated monophosphoryl lipid A (3D-MPL) and/or polyoxyethylene sorbitan trioleate (such as SPAN 85). Additionally the preferred form of 3 De-O-acylated monophosphoryl lipid A is disclosed in International patent application published under No. 92116556—SmithKline Beecham Biologicals s.a.

Preferably the vaccine formulations of the present invention contain an antigen or antigenic composition capable of eliciting an immune response against a human pathogen, which antigen or antigenic composition is derived from HIV-1, (such as tat, nef, gp120 or gp160), human herpes viruses, such as gD or derivatives thereof or Immediate Early protein such as ICP27 from HSV1 or HSV2, cytomegalovirus ((esp Human)(such as gB or derivatives thereof), Rotavirus (including live-attenuated viruses), Epstein Barr virus (such as gp350 or derivatives thereof), Varicella Zoster Virus (such as gpI, II and IE63), or from a hepatitis virus such as hepatitis B virus (for example Hepatitis B Surface antigen or a derivative thereof), hepatitis A virus, hepatitis C virus and hepatitis E virus, or from other viral pathogens, such as paramyxoviruses: Respiratory Syncytial virus (such as F and G proteins or derivatives thereof), parainfluenza virus, measles virus, mumps virus, human papilloma viruses (for example HPV6, 11, 16, 18, . . . ), flaviviruses (e.g. Yellow Fever Virus, Dengue Virus, Tick-borne encephalitis virus, Japanese Encephalitis Virus) or Influenza virus, or derived from bacterial pathogens such as Neisseria spp, including *N. gonorrhea* and *N. meningitidis* (for example capsular polysaccharides and conjugates thereof, transferrin-binding proteins, lactoferrin binding proteins, PilC, adhesins); Streptococcus spp, including *S. pneumoniae* (for example capsular polysaccharides and conjugates thereof, PsaA, PspA, streptolysin, choline-binding proteins), *S. pyogenes* (for example M proteins or fragments thereof, C5A protease, lipoteichoic acids), *S. agalactiae, S. mutans*; Haemophilus spp, including *H. influenzae* type B (for example PRP and conjugates thereof), non typeable *H. influenzae* (for example OMP26, high molecular weight adhesins, P5, P6, lipoprotein D), *H. ducreyi*; Moraxella spp, including *M catarrhalis*, also known as *Branhamella catarrhalis* (for example high and low molecular weight adhesins and invasins); Bordetella spp, including *B. pertussis* (for example pertactin, pertussis toxin or derivatives thereof, filamenteous hemagglutinin, adenylate cyclase, fimbriae), *B. parapertussis* and *B. bronchiseptica*; Mycobacterium spp., including *M. tuberculosis* (for example ESAT6, Antigen 85A, -B or -C), *M. bovis, M. leprae, M. avium, M. paratuberculosis, M. smegmatis*; Legionella spp, including *L. pneumophila*; Escherichia spp, including enterotoxic *E. coli* (for example colonization factors, heat-labile toxin or derivatives thereof, heat-stable toxin or derivatives thereof), enterohemorragic *E. coli*, enteropathogenic *E. coli* (for example shiga toxin-like toxin or derivatives thereof); Vibrio spp, including *V. cholera* (for example cholera toxin or derivatives thereof), Shigella spp, including *S. sonnei, S. dysenteriae, S. flexnerii*; Yersinia spp, including *Y. enterocolitica* (for example a Yop protein), *Y. pestis, Y. pseudotuberculosis*, Campylobacter spp, including *C. jejuni* (for example toxins, adhesins and invasins) and *C. coli*; Salmonella spp, including *S. typhi, S. paratyphi, S. choleraesuis, S. enteritidis*; Listeria spp., including *L. monocytogenes*; Helicobacter spp, including *H. pylori* (for example urease, catalase, vacuolating toxin); Pseudomonas spp, including *P. aeruginosa*, Staphylococcus spp., including *S. aureus, S. epidermidis*; Enterococcus spp., including *E. faecalis, E. faecium*; Clostridium spp., including *C. tetani* (for example tetanus toxin and derivative thereof), *C. botulinum* (for example botulinum toxin and derivative thereof, *C. difficile* (for example clostridium toxins A or B and derivatives thereof); Bacillus spp., including *B. anthracis* (for example botulinum toxin and derivatives thereof); Corynebacterium spp., including *C. diphtheriae* (for example diphtheria toxin and derivatives thereof); Borrelia spp., including *B. burgdorferi* (for example OspA, OspC, DbpA, DbpB), *B. garinii* (for example OspA, OspC, DbpA, DbpB), *B. afzelii* (for example OspA, OspC, DbpA, DbpB), *B. andersonii* (for example OspA, OspC, DbpA, DbpB), *B. hermsii*; Ehrlichia spp., including *E. equi* and the agent of the Human Granulocytic Ehrlichiosis; Rickettsia spp, including *R. rickettsii*; Chlamydia spp., including *C. trachomatis* (for example MOMP, heparin-binding proteins), *C. neumoniae* (for example MOMP, heparin-binding proteins), *C. psittaci*; Leptospira spp., including *L. interrogans*; Treponema spp., including *T. pallidum* (for example the rare outer membrane proteins), *T. denticola, T. hyodysenteriae*; or derived from parasites such as Plasmodium spp., including *P. faiciparum*; Toxoplasma spp., including *T. gondii* (for example SAG2, SAG3, Tg34); Entamoeba spp., including *E. histolytica*; Babesia spp., including *B. microti*; Trypanosoma spp., including *T. cruzi*; Giardia spp., including *G. lamblia*; Leshmania spp., including *L. major*; Pneumocystis spp., including *P. carinii*; Trichomonas spp., including *T. vaginalis*; Schisostoma spp., including *S. mansoni*, or derived from yeast such as Candida spp., including *C. albicans*; Cryptococcus spp., including *C. neoformans*.

Derivatives of Hepatitis B Surface antigen are well known in the art and include, inter alia, those PreS1, PreS2 S antigens set forth described in European Patent applications EP-A-414 374; EP-A-0304 578, and EP 198-474. In one preferred aspect the vaccine formulation of the invention comprises the HIV-1 antigen, gp120, especially when expressed in CHO cells. In a further embodiment, the vaccine formulation of the invention comprises gD2t as hereinabove defined.

In a preferred embodiment of the present invention vaccines containing the claimed adjuvant comprise the HPV viruses considered to be responsible for genital warts, (HPV6 or HPV11 and others), and the HPV viruses responsible for cervical cancer (HPV16, HPV18 and others). Particularly preferred forms of vaccine comprise L1 particles or capsomers, and fusion proteins comprising one or more antigens selected from the HPV 6 and HPV11 proteins E6, E7, L1, and L2. The most preferred forms of fusion protein are: L2E7 as disclosed in GB 95 15478.7, and proteinD(1/3)-E7 disclosed in GB 9717953.5.

Vaccines of the present invention further comprise antigens derived from parasites that cause Malaria. For example, preferred antigens from *Plasmodia falciparum* include RTS,S and TRAP. RTS is a hybrid protein comprising substantially all the C-terminal portion of the circunsporozoite (CS) protein of *P. falciparum* linked via four amino acids of the preS2 portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S. TRAP antigens are described in the International Patent Application No. PCT/GB89/00895, published under WO 90/01496. A preferred embodiment of the present invention is a Malaria vaccine wherein the antigenic preparation comprises a combination of the RTS,S and TRAP antigens. Other plasmodia antigens that are likely candidates to be components of a multistage Malaria vaccine are *P. faciparum* MSP1, AMA1, MSP3, EBA, GLURP, RAP1, RAP2, Sequestrin, PfEMP1, Pf332, LSA1, LSA3, STARP, SALSA, PfEXP1, Pfs25, Pfs28, PFS27/25, Pfs16, Pfs48/45, Pfs230 and their analogues in Plasmodium spp.

The formulations may also contain an anti-tumor antigen and be useful for the immunotherapeutic treatment of cancers. For example, the adjuvant formulation finds utility with tumor rejection antigens such as those for prostrate, breast, colorectal, lung, pancreatic, renal or melanoma cancers. Exemplary antigens include MAGE 1 and MAGE 3 or other MAGE antigens for the treatment of melanoma, PRAME, BAGE or GAGE (Robbins and Kawakami, 1996, Current Opinions in Immunology 8, pps 628–636; Van den Eynde et al., International Journal of Clinical & Laboratory Research (submitted 1997); Correale et al. (1997), Journal of the National Cancer Institute 89, p293. Indeed these antigens are expressed in a wide range of tumor types such as melanoma, lung carcinoma, sarcoma and bladder carcinoma. Other Tumor-Specific antigens are suitable for use with adjuvant of the present invention and include, but are not restricted to Prostate specific antigen (PSA) or Her-2/neu, KSA (GA733), MUC-1 and carcinoembryonic antigen (CEA). Accordingly in one aspect of the present invention there is provided a vaccine comprising an adjuvant composition according to the invention and a tumor rejection antigen.

It is foreseen that compositions of the present invention will be used to formulate vaccines containing antigens derived from Borrelia sp. For example, antigens may include nucleic acid, pathogen derived antigen or antigenic preparations, recombinantly produced protein or peptides, and chimeric fusion proteins. In particular the antigen is OspA. The OspA may be a full mature protein in a lipidated form virtue of the host cell (E.Coli) termed (Lipo-OspA) or a non-lipidated derivative. Such non-lipidated derivatives include the non-lipidated NS1-OspA fusion protein which has the first 81 N-terminal amino acids of the non-structural protein (NS1) of the influenza virus, and the complete OspA protein, and another, MDP-OspA is a non-lipidated form of OspA carrying 3 additional N-terminal amino acids.

Vaccines of the present invention may be used for the prophylaxis or therapy of allergy. Such vaccines would comprise allergen specific (for example Der p1) and allergen non-specific antigens (for example the stanworth decapeptide).

The ratio of the QS21 to cholesterol (w/w), present in a preferred embodiment of the present invention, is envisaged to be in the range of 1:1 to 1:20, substantially 1:10.

The ratio of QS21:3D-MPL (w/w) will typically be in the order of 1:10 to 10:1; preferably 1:5 to 5:1 and often substantially 1:1. The preferred range for optimal synergy is 2.5:1 to 1:1 3D MPL: QS21. Typically for human administration QS21 and 3D MPL will be present in a vaccine in the range 1 $\mu$g–100 $\mu$g, preferably 10 $\mu$g–50 $\mu$g per dose. Typically the oil in water will comprise from 2 to 10% squalene, from 2 to 10% α-tocopherol and from 0.4 to 2% polyoxyethylene sorbitan monooleate (TWEEN 80). Preferably the ratio of squalene: α-tocopherol is equal or less than 1 as this provides more stable emulsion. Sorbitan trioleate (SPAN 85) may also be present at a level of 0.5 to 1%. In some cases it may be advantageous that the vaccines of the present invention will further contain a stabiliser, for example other emulsifyers/surfactants, including Caprylic acid (merck index 10th Edition, entry no.1739), of which Tricaprylin is a particularly preferred embodiment.

Vaccine preparation is generally described in New Trends and Developments in Vaccines, edited by Voller et al., University Park Press, Baltimore, Md., U.S.A. 1978. Conjugation of proteins to macromolecules is disclosed by Likhite, U.S. Pat. No. 4,372,945 and by Armor et al., U.S. Pat. No. 4,474,757.

The amount of protein in each vaccine dose is selected as an amount which induces an immunoprotective response without significant, adverse side effects in typical vaccinees. Such amount will vary depending upon which specific immunogen is employed and how it is presented. Generally, it is expected that each dose will comprise 1–1000 $\mu$g of protein, preferably 1–500 $\mu$g, preferably 1–100 $\mu$g, of which 1 to 50 $\mu$g is the most preferable range. An optimal amount for a particular vaccine can be ascertained by standard studies involving observation of appropriate immune responses in subjects. Following an initial vaccination, subjects may receive one or several booster immunisations adequately spaced.

The compositions of the present invention can be used to formulate vaccines containing antigens derived from a wide variety of sources. For example, antigens may include human, bacterial, or viral nucleic acid, pathogen derived antigen or antigenic preparations, tumour derived antigen or antigenic preparations, host-derived antigens, including the histamine releasing decapeptide of IgE (known as the Stanworth decapeptide), recombinantly produced protein and peptides, and chimeric fusion proteins.

In a further aspect of the present invention there is provided a vaccine as herein described for use in medicine.

Also provided by the present invention is a method of quenching the reactogenicity of a saponin, preferably QS21, containing oil in water emulsion, comprising the addition of a sterol, preferably cholesterol, into the oil phase of the oil in water emulsion.

QS21 in aqueous solution is known to degenerate over time into an adjuvant-inactive form, QS21-H, which degeneration is mediated by $^-$OH hydrolysis by the aqueous medium. Such degeneration may occur when the QS21 is present in the aqueous phase of an oil in water adjuvant. Surprisingly it has been found that the addition of cholesterol to the oil phase of the oil in water emulsion has the effect of maintaining the QS21 in its active form, with obvious benefits to the shelf-life of the adjuvant/vaccine formulation. The present invention provides a method of stablilising a preparation of a saponin, preferably QS21, in its non-hydrolysed adjuvant-active form, when the QS21 is present in an oil in water emulsion based adjuvant. This method comprises the addition of a sterol, preferably cholesterol, into the oil phase of an oil in water emulsion.

Also provided by the present invention is the process for the production of an adjuvant or vaccine preparation comprising the addition of cholesterol to a metabolisable oil, followed by emulsification of the oil phase; into which emulsion is added QS21, and optionally 3D-MPL, α-tocopherol, and antigen.

The vaccine preparation of the present invention may be used to protect or treat a mammal susceptible to, or suffering from a disease, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts.

EXAMPLE 1

Preparation of the Oil in Water Emulsion Adjuvants

The oil in water emulsion adjuvant formulations used in the subsequent examples were each made comprising the following oil in water emulsion component: 5% Squalene, 5% α-tocopherol, 2.0% polyoxyethylene sorbitan monooleate (TWEEN 80).

The emulsion was prepared as follows as a 2 fold concentrate. All examples used in the immunological experiments are diluted with the addition of extra components and diluents to give either a 1× concentration (equating to a squalene:QS21 ratio (w/w) of 240:1) or further dilutions thereof.

Briefly, the TWEEN 80 is dissolved in phosphate buffered saline (PBS) to give a 2% solution in the PBS. To provide 100 ml of a two fold concentrate emulsion, 5 ml of DL alpha tocopherol and 5 ml of squalene are vortexed to mix thoroughly. 95 ml of PBS/Tween solution is added to the oil and are mixed thoroughly. The resulting emulsion is then passed through a syringe needle and finally microfluidised by using an M110S Microfluidics machine. The resulting oil droplets have a size of approximately 145–180 nm (expressed as z av. measured by PCS) and is termed "full dose" SB62.

These formulations can be sterile filtered through a 0.24 μm filter. The other adjuvant/vaccine components (QS21, 3D-MPL or antigen) are added to the emulsion in simple admixture.

The antigen containing vaccines used herein are formulated either with full dose SB62 adjuvant to give a high squalene:QS21 ratio (240:1) or with a lower amount of emulsion to give a low ratio formulation (48:1), these adjuvant formulations are called SB62 and SB62' respectively. Other vaccines were formulated with the addition of cholesterol to the oil phase of the emulsion prior to the emulsifying process, wherein the QS21:cholesterol ratio of 1:10 (denoted by the addition of the letter "c").

EXAMPLE 2

Reactogenicity Studies with Vaccines Comprising Oil in Water Emulsions and QS21 with the Optional Addition of Cholesterol A study was conducted to examine the local and systemic reactogenicity of various vaccine formulations containing the Herpes Simplex Virus (HSV) glycoprotein gD2t. Oil in water vaccine (o/w) adjuvants containing QS21 are known to produce moderate adverse effects upon administration to a host. This study compared the reactogenic profile resulting from vaccination with a gD2t/o/w vaccine, with that from the same vaccine formulations which further contained cholesterol.

Reactogenicity Study Experimental Procedure

Groups of 5 SPF bred New Zealand White albino rabbits were inoculated by intramuscular injection into the right hind leg muscle (gastrocnemius), with 0.5 ml of the adjuvant preparations (for details of production see example 1). Samples were taken before and after vaccination to assay the percentage blood polymorpho-neutrophils (as a measure of inflammation, %PMN), and Creatine phosphokinase (as a measure of muscle damage, CPK). The animals were sacrificed 3 days after vaccination for histological examination of the injection site.

TABLE 1

Groups of animals and formulations used in example 2.

| | | | Adjuvant formulation | | | | |
|---|---|---|---|---|---|---|---|
| Group | Antigen gD2t (μg) | MPL (μg) | QS21 (μg) | SB62 (μl) | Chol (μg) | PBS (μl) | o/w dose |
| 1 | 20 | 50 | 50 | 250 | — | 250 | 1/1 |
| 2 | 20 | 50 | 50 | 125 | — | 375 | 1/2 |
| 3 | 20 | 50 | 50 | 83.3 | — | 416.7 | 1/3 |
| 4 | 20 | 50 | 50 | 62.5 | — | 437.5 | 1/4 |
| 5 | 20 | 50 | 50 | 50 | — | 450 | 1/5 |
| 6 | — | — | — | — | — | 500 | — |
| 7 | 20 | 50 | 50 | 250 | 500 | 250 | 1/1 |
| 8 | 20 | 50 | 50 | 125 | 500 | 375 | 1/2 |
| 9 | 20 | 50 | 50 | 83.3 | 500 | 416.7 | 1/3 |
| 10 | 20 | 50 | 50 | 62.5 | 500 | 437.5 | 1/4 |

TABLE 1-continued

Groups of animals and formulations used in example 2.

| | | | Adjuvant formulation | | | | |
|---|---|---|---|---|---|---|---|
| Group | Antigen gD2t (μg) | MPL (μg) | QS21 (μg) | SB62 (μl) | Chol (μg) | PBS (μl) | o/w dose |
| 11 | 20 | 50 | 50 | 50 | 500 | 450 | 1/5 |
| 12 | — | — | — | — | — | 500 | — | footnotes:
SB62 = full dose oil in water emulsion
PBS = Phosphate Buffered Saline In this experiment the vaccine preparation in group 1 the SB62 stock preparation is diluted with the addition of extra components and diluents to give a 1× concentration (1/1). In other groups the SB62 final dilution varies between 1/2 to 1/5. Groups 1 to 5 lene:QS21 ratio (w/w) of 240:1, 120:1, 80:1, 60:1 and 48:1 respectively.

The antigen used in this study is a truncated HSV-2 glycoprotein D of 308 amino acids, which comprises amino acids 1 through 306 naturally occurring glycoprotein with the addition Aspragine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells has been described in Genentech's European patent EP-B-139 417. The antigen is used in the vaccine formulations of the present invention as is designated gD$_2$t.

CPK levels, in units per litre (U/L), were determined from serum at various time points throughout the experiment, using commercially available reagents (Abbot) and a Abbot Vision System analyser. Levels of PMN in blood samples were determined concurrently using a Sysmex K-1000 Haematology analyser (Toa Medical Electronics Co.).

Reactogenicity Results
CPK Levels

TABLE 2

CPK concentrations pre and post injection.

| | Mean CPK (U/L) | | |
|---|---|---|---|
| Group | Day 0 (SD) | Day 1 (SD) | Day 3 (SD) |
| 1 | 1093(202) | 3308(2013) | 1995(1047) |
| 2 | 818(215) | 3701(1430) | 1842(915) |
| 3 | 784(228) | 3346(1434) | 2321(780) |
| 4 | 946(228) | 2963(1246) | 2316(593) |
| 5 | 808(686) | 3976(1311) | 1963(1177) |
| 6 | 726(163) | 769(107) | 1208(388) |
| 7 | 1687(527) | 994(541) | 1667(249) |
| 8 | 1006(309) | 836(469) | 1408(1113) |
| 9 | 1367(536) | 1012(462) | 1171(503) |
| 10 | 899(373) | 1083(737) | 731(282) |
| 11 | 1137(310) | 952(257) | 1610(441) |
| 12 | 1086(713) | 1078(321) | 1475(1642) |

From table 2, it is clear that when cholesterol was added to these formulations, no muscle damage was observed in terms of CPK. CPK levels were substantially the same as, or lower than, those seen before vaccination or after vaccination with PBS. Vaccine preparations not containing cholesterol induced a significant increases in blood CPK levels on day 1. These CPK levels were independent of SB62 dilution.

% PMN Results

The results relating to the %PMN observed after vaccination can be summarised by the following. A transient PMN burst was observed on day 1 in all animals injected, independent of SB62 dilution and presence of cholesterol.

Conclusions

The addition of cholesterol suppresses the reactogenicity in terms of muscle damage of QS21/o/w emulsion adjuvant formulations.

The addition of cholesterol did not influence the induction of the desirable inflammatory response. The effect on the CPK levels and PMN burst effect was independent of the amount of o/w emulsion present in the vaccine formulation.

EXAMPLE 3

Immunogenicity Studies in Mice with the Glycoprotein gD2t from HSV

A study was conducted in Balb/C mice with oil in water emulsion vaccine formulations using the Herpes Simplex Virus glycoprotein gD2t as the antigen. The study investigated the induction of gD2t specific humoral and cellular immune responses (cytokine production and cellular proliferation), and investigated the consequences of the addition of cholesterol to the formulation.

Groups of 10 Balb/C mice were immunised in the rear footpads (50 μg per footpad) with the following formulations, at days 0 and 28:

TABLE 3

Groups of mice and vaccine formulations used in example 3.

| Group | Vaccine formulation |
| --- | --- |
| 13 | gD2t (2 μg)/3D-MPL(5 μg)/QS21(5 μg)/SB62(25 μl) |
| 14 | gD2t (2 μg)/3D-MPL(5 μg)/QS21(5 μg)/SB62(25 μl)/Cholesterol(50 μg) |
| 15 | gD2t (2 μg)/3D-MPL(5 μg)/Alum(50 μg) |

The vaccines were prepared using the SB62 oil in water emulsion adjuvants as described in example 1. The antigen used in this study is a truncated HSV-2 glycoprotein D of 308 amino acids, which comprises amino acids 1 through 306 naturally occurring glycoprotein with the addition Asparagine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells has been described in Genentech's European patent EP-B-139 417. The antigen is used in the vaccine formulations of the present invention as is designated gD$_2$t.

Serology

Sera was obtained from 5 mice from each group at 14 days after the second immunisation, and again from the 5 remaining mice 28 days after the second immunization. Each serum sample was tested in ELISA for anti-gD2t Ig titers and the isotype distribution using pooled sera was measured.

Cytokine Production

Spleen and lymph node cells were also isolated 14 and 28 days (n=5) after the second immunisation. Pooled samples were analysed for both gD2t-specific proliferation and cytokine (IFN-γ and IL-5) secretion.

Results from the Mouse Studies

The results from the mice immunised with the gD2t vaccines are summarised in the following table. The magnitude of the response with respect to each parameter measured is indicated by the number of "+" signs.

TABLE 4

Summary table showing the anti-gD2t immune responses in mice (example 3).

| | Serology | | Cytokine production | |
| --- | --- | --- | --- | --- |
| Group | IgG | IgG 2a and b | IL-5 | IFN-γ |
| 13 | ++++ | ++ | + | ++ |
| 14 | ++++ | +++ | + | ++ |
| 15 | ++ | + | ++ | + |

The addition of cholesterol did not, therefore, effect the magnitude or quality of the anti-gD2t immune responses in the murine model.

EXAMPLE 4

Immunogenicity Studies in Rhesus Monkeys with the Glycoprotein gD2t from HSV

Groups of 5 rhesus monkeys were immunised intramuscularly in the posterior part of the right leg (500 μl) with the following vaccine formulations:

TABLE 5

Vaccine formulations used in the Rhesus monkey model (example 4).

| Group | Vaccine formulation |
| --- | --- |
| 16 | gD2t (20 μg)/3D-MPL(50 μg)/QS21(50 μg)/SB62(250 μl) |
| 17 | gD2t (20 μg)/3D-MPL(50 μg)/QS21(50 μg)/SB62(250 μl)/Cholesterol(500 μg) |
| 18 | gD2t (20 μg)/3D-MPL(50 μg)/Alum(500 μg) |

The vaccines were prepared using the SB62 emulsion adjuvants as described in example 1. The antigen used in this study is a truncated HSV-2 glycoprotein D of 308 amino acids, which comprises amino acids 1 through 306 naturally occurring glycoprotein with the addition Asparagine and Glutamine at the C terminal end of the truncated protein devoid of its membrane anchor region. This form of the protein includes the signal peptide which is cleaved to yield a mature 283 amino acid protein. The production of such a protein in Chinese Hamster ovary cells has been described in Genentech's European patent EP-B-139 417. The antigen is used in the vaccine formulations of the present invention as is designated gD$_2$t.

The monkeys were vaccinated on days 0, 28 and 84. Serum was taken from each monkey at 14, 28, and 42 days after the third vaccination. Each serum was tested in ELISA for anti-gD2t Ig titres. Results were expressed as ELISA units (EU). Neutralisation assays were also performed, which evaluated the ability of serial dilutions of the sera to neutralise in vitro the infectivity of HSV-2 (strain HG-52). Results were expressed as mid-point titres after regression analysis.

A DTH test was performed at 42 days after the third vaccination. 28 μg gD2t diluted in PBS (total volume of 100μl) was injected intradermally in duplicate. Controls consisted of PBS alone. Skin thickness was measured prior to, and 24 hours after, injection. Data was expressed as specific increase of skin thickness (difference between the site injected with gD2t and the site injected with PBS).

Results from the Rhesus Monkey Studies

The results from the Rhesus monkeys immunised with the gD2t vaccines are summarised in the following table (data shown is the mean from the 5 monkeys).

TABLE 6

Summary table showing the anti gD2t immune responses induced in Rhesus monkeys.

| Group | Serum anti-gD2t titre (14d post VII)* | Neutralisation titre (28d post VIII)* | DTH (mm)** |
|---|---|---|---|
| 16 | 14,000 | 900 | 0.9 |
| 17 | 16,000 | 800 | 1 |
| 18 | 4000 | 400 | 1.1 |

*geometric mean titre of the group
**average of the group

Conclusions

Both of the SB62 based vaccine formulations induced very high titres of anti-gD2t antibodies in the monkeys. Furthermore, these vaccines also induced neutralising antibody and stimulated DTH responses. The inclusion of cholesterol had no effect on the performance of the vaccines.

EXAMPLE 5

Reactogenicity Studies with Oil in Water Emulsion Adjuvants with QS21 with the Optional Addition of Cholesterol A study was conducted to examine the local and systemic reactogenicity of various adjuvant formulations. Oil in water vaccine adjuvants containing QS21 are known to produce moderate adverse clinical symptoms upon administration to a host. This study compared the resultant reactogenic profile with that resulting from the same adjuvant formulations which further contained cholesterol.

Experimental Procedure

The oil in water emulsions tested were produced using techniques described in example 1. Groups of 5 SPF bred New Zealand White albino rabbits were inoculated by intramuscular injection into the right hind leg muscle (gastrocnemius), with 0.5 ml of the adjuvant preparations. Samples were taken before and after vaccination to assay the percentage blood polymorpho-neutrophils (as a measure of inflammation, %PMN), and Creatine phosphokinase (as a measure of muscle damage, CPK). The animals were sacrificed 3 days after vaccination for histological examination of the injection site.

TABLE 7

Groups of rabbits used in example 5.:

| Group | Vaccine preparation |
|---|---|
| 19 | SB62', QS21(50 μg), MPL(50 μg) |
| 20 | SB62'c, QS21(50 μg), MPL(50 μg) |
| 21 | QS21(50 μg) |
| 22 | QS21(5 μg) |
| 23 | SB62 |
| 24 | SB62c |
| 25 | PBS | footnotes:
SB62 = full dose oil in water emulsion
SB62' = 1/5th dose SB62
SB62'c = SB62' containing cholesterol in the oil phase
PBS = Phosphate Buffered Saline CPK levels, in units per litre (U/L), were determined from serum at various time points throuhout the experiment, using commercially available reagents (Abbot) and a Abbot Vision Systems analyser. % PMN in blood samples were determined concurrently using a Sysmex K-1000 Haematology analyser (Toa Medical Electronics Co.).

Three days after injection post-mortem inspection of the rabbits determined lesion size at injection site, and local histopathology.

Results
CPK Levels Pre and Post Vaccination

TABLE 8

Mean CPK concentrations in Rabbits

| | Mean CPK (U/L) | | |
|---|---|---|---|
| Group | Day 0 (SD) | Day 1 (SD) | Day 3 (SD) |
| 19 | 764 (545) | 2868 (1284) | 1539 (487) |
| 20 | 1364 (1842) | 871 (543) | 1360 (309) |
| 21 | 400 (191) | 2860 (1405) | 1364 (552) |
| 22 | 962 (783) | 1650 (343) | 1370 (475) |
| 23 | 863 (762) | 719 (306) | 1164 (426) |
| 24 | 606 (274) | 599 (172) | 1336 (779) |
| 25 | 401 (107) | 778 (176) | 666 (164) |

From Table 8, above, it can be seen that adjuvant formulations containing QS21 show a marked increase in plasma CPK levels 1 day after injection, indicating a significant level of muscle damage at the site of injection (groups 19, 21, and 22).

The addition of cholesterol to the adjuvant formulation quenches this effect and as such no increases in CPK are seen after vaccination (group 20). The results attained using this adjuvant are very similar to those obtained with PBS or SB62 given alone (see groups 23, 24, and 25).

Percentage PMN
Table 9, Changes in Blood % PMN

TABLE 9 changes in blood % PMN

| | % PMN | | | | |
|---|---|---|---|---|---|
| Group | Day-5 (SD) | Day-1 (SD) | Day 0 (SD) | Day 1 (SD) | Day 3 (SD) |
| 19 | 14.1 (2.1) | 18.9 (2.1) | 15.2 (1.8) | 34.0 (4.6) | 12.9 (1) |
| 20 | 17.3 (1.1) | 20.7 (3.2) | 18.0 (2.8) | 40.2 (8.4) | 16.7 (3.9) |
| 21 | 15.8 (1.9) | 18.4 (1.6) | 15.6 (1.3) | 25.7 (5.6) | 14.3 (2.2) |
| 22 | 14.3 (2.3) | 16.3 (2.2) | 14.7 (1.9) | 14.6 (3.2) | 15.9 (2.7) |
| 23 | 15.5 (1.2) | 16.5 (1.4) | 15.7 (2.1) | 31.9 (7.1) | 14.0 (3.2) |
| 24 | 16.5 (1.7) | 20.0 (2.7) | 13.6 (2.6) | 32.3 (2.7) | 14.9 (2.5) |
| 25 | 15.0 (2.9) | 18.2 (2.9) | 16.4 (2.2) | 16.1 (5.0) | 12.4 (2.2) |

The percentage of blood PMN is taken to be a readout of the magnitude of the local inflammation reaction in response to vaccination. As can be seen from table 9, the addition of cholesterol to the QS21 containing adjuvant formulation does not significantly affect the inflammatory process at day 1 post-vaccination, despite the absence of muscle damage as indicated in table 8. The addition of cholesterol does not affect the inflammatory process induced by SB62.

TABLE 10

Histological examination

| Group | Rabbit | les | Site of injection size (mm) | necro | rhabdo | infiltr | oedem | haemo | Remark |
|---|---|---|---|---|---|---|---|---|---|
| 19 | 1 | + | 3 × 3 × 2 | 1 | 1 | 3 | 2 | 2 | |
| | 2 | + | 30 × 10 × 6 | 4 | 2 | 3 | 2 | 2 | |
| | 3 | + | 25 × 18 × 6 | 4 | 3 | 3 | 2 | 3 | |
| | 4 | + | 28 × 10 × 5 | 4 | 2 | 3 | 2 | 3 | |
| | 5 | + | 27 × 14 × 4 | 4 | 2 | 3 | 2 | 2 | |
| 20 | 6 | + | 3 × 2 × 2 | 1 | 2 | 3 | 1 | 2 | |
| | 7 | s | 0 | 0 | 0 | 1 | 0 | 0 | |
| | 8 | − | 0 | 1 | 0 | 1 | 0 | 0 | |
| | 9 | − | 0 | 1 | 2 | 2 | 1 | 1 | |
| | 10 | + | 4 × 2 × 2 | 1 | 2 | 3 | 1 | 2 | |
| 21 | 11 | + | 24 × 13 × 5 | 4 | 2 | 3 | 2 | 3 | |
| | 12 | + | 25 × 12 × 7 | 4 | 3 | 3 | 2 | 3 | |
| | 13 | + | 22 × 12 × 4 | 4 | 2 | 3 | 2 | 3 | |
| | 14 | + | 18 × 10 × 4 | 4 | 2 | 3 | 2 | 3 | |
| | 15 | + | 22 × 12 × 7 | 4 | 3 | 3 | 2 | 3 | |
| 22 | 16 | + | 14 × 7 × 5 | 3 | 3 | 3 | 2 | 3 | |
| | 17 | + | 8 × 4 × 2 | 3 | 2 | 3 | 2 | 4 | |
| | 18 | + | 10 × 8 × 3 | 3 | 1 | 3 | 2 | 1 | |
| | 19 | + | 4 × 3 × 2 | 2 | 2 | 3 | 2 | 4 | |
| | 20 | + | 12 × 7 × 2 | 2 | 3 | 3 | 2 | 3 | |
| 23 | 21 | − | 0 | 0 | 2 | 2 | 1 | 1 | |
| | 22 | s | 0 | 0 | 1 | 2 | 1 | 1 | |
| | 23 | − | 0 | 0 | 0 | 1 | 0 | 0 | |
| | 24 | − | 0 | 0 | 0 | 0 | 0 | 0 | |
| | 25 | − | 0 | 0 | 0 | 0 | 0 | 0 | |
| 24 | 26 | − | 0 | 0 | 1 | 2 | 0 | 0 | |
| | 27 | s | 0 | 0 | 1 | 2 | 0 | 0 | |
| | 28 | − | 0 | 0 | 1 | 2 | 0 | 0 | |
| | 29 | − | 0 | 0 | 0 | 2 | 0 | 0 | |
| | 30 | s | 0 | 1 | 2 | 2 | 1 | 1 | |
| 25 | 31 | s | 0 | 0 | 0 | 1 | 0 | 0 | |
| | 32 | s | 0 | 0 | 0 | 0 | 0 | 0 | |
| | 33 | s | 0 | 0 | 0 | 2 | 1 | 1 | |
| | 34 | − | 0 | 0 | 0 | 0 | 0 | 0 | |
| | 35 | − | 0 | 0 | 0 | 0 | 0 | 0 | | footnotes:
les = lesion
necro = necrosis
infiltr = lymphocytic infiltration
oedem = oedema
haemo = haemorrhage
rhabdo = rhabdomyolosis
Gradation: 0 = no sign
1 = very slight
2 = slight
3 = moderate
4 = severe
+ = present
s = spot
− = no sign Histological examination at the site of injection confirms the earlier CPK data shown in table 8, in that local damage was reduced significantly by the addition of cholesterol into the adjuvant formulation.

Severe necrosis, accompanied with moderate rhabdomyolosis oedema and haemorrhage was observed with all vaccine adjuvants containing "unquenched" QS21 (groups 19, 21, and 22) These signs were associated with very large lesions at the site of injection.

The inclusion of cholesterol (group 20) reduced the macroscopical appearence of lesions (in only 2 of the 5 rabbits) when compared to those observed in group 19, and significantly reduced the severity of other histopathological signs when present.

Conclusions

It is clear from the results described above that the use of the adjuvant formulations comprising QS21, or indeed QS21 alone, cause a significant amount of local damage at the site of injection. This deleterious effect can be successfully abrogated by the inclusion of cholesterol to the adjuvant formulation.

EXAMPLE 6

Immunogenicity Studies with Malaria Antigens TRAP and RTS,S

Immunisation experiments using the *Plasmodium falciparum* Malaria antigens TRAP and RTS,S in combination with various adjuvants, each based on an oil in water emulsion system. RTS is a hybrid protein comprising substantially all the C-terminal portion of the circumsporozoite (CS) protein of *P. falciparum* linked via four amino acids of the $preS_2$ portion of Hepatitis B surface antigen to the surface (S) antigen of hepatitis B virus. It's full structure is disclosed in the International Patent Application No. PCT/EP92/02591, published under Number WO 93/10152 claiming priority from UK patent application No.9124390.7. When expressed in yeast RTS is produced as a lipoprotein particle, and when it is co-expressed with the S antigen from HBV it produces a mixed particle known as RTS,S.

TRAP antigens are described in the International Patent Application No. PCT/GB89/00895, published under WO 90/01496. TRAP antigens are polypeptides, so called Thrombospondin Related Anonymous Proteins, which share homology with various *P. falciparum* proteins.

Various formulations with two different squalene:QS21 ratios, optionally with cholesterol at a QS21 cholesterol ratio (w/w) of 1:10, were combined with the malaria antigens and compared in their ability to induce humoral and cell mediated immune responses (T-cell proliferation and cytokine production). These formulations were produced using the techniques described in example 1.

Groups of 5 mice (six weeks old female mice, strain C57/BL6×CBA/J [H-2k]) were immunised twice (in 2×5 $\mu$l volumes) in the hind foot-pad, 14 days apart, with either 10 $\mu$g RTS,S or 4 $\mu$g TRAP combined with various oil in water emulsion systems (SB62). 14 days following the second imnnunisation the production of cytokines (IL5 and IFN-$\gamma$) and T-cell proliferation was analysed after in vitro restimulation of spleen and lymph nodes cells with the malaria antigens. Antibody response to RTS,S and TRAP and the isotypic profile that was induced was investigated by ELISA.

TABLE 11

Animal Groups

| Group No. | Antigen | Adjuvant |
|---|---|---|
| 26 | RTS,S | SB62/QS21/3D-MPL |
| 27 | TRAP | SB62/QS21/3D-MPL |
| 28 | RTS,S/TRAP | SB62/QS21/3D-MPL |
| 29 | RTS,S | A1OH/QS21/3D-MPL |
| 30 | RTS,S/TRAP | A1OH/QS21/3D-MPL |
| 31 | RTS,S | SB62c/QS21/3D-MPL |
| 32 | RTS,S/TRAP | SB62c/QS21/3D-MPL |
| 33 | RTS,S | SB62'/QS21/3D-MPL |
| 34 | RTS,S/TRAP | SB62'/QS21/3D-MPL |
| 35 | — | SB62/QS21/3D-MPL |
| 36 | Vac.Vir. 3D7 | |

Footnotes:
SB62-oil in water emulsion full dose
SB62'-oil in water emulsion exemplified in the figures as SB62 1/5th dose
SB62c or SB62'c-oil in water emulsion (either dose) plus cholesterol in the oil phase.
Vac.Vir. 3D7 = a recombinant vaccinia virus construct expressing CS protein and administered at $10^6$PFU per mouse.

Methology
T-cell Proliferation

Spleen or popliteal lymph node cells were aseptically removed and washed. 100 $\mu$l of cells in RPMI medium (1% heat-inactivated normal mouse serum, NMS) containing 2×10$^6$/ml of cells were cultured in round bottomed plates in the presence of RTS,S or TRAP antigens. Following stimulation for 96 hours with 0.1, 0.5, and 2.5 82 g of antigen, or 48 hours with 2 $\mu$g/ml ConA, the cells were labelled with $^3$H-Thymidine (1 $\mu$Ci/well) for 16 hours before harvesting and counting in a $\beta$-counter.
RPMI Medium:

RPMI 1640 without L-glutamine (Life technologies No.31870025), 2 mM L-glutamine (Life technologies No.25030024), 50$\mu$M 2-Mercaptoethanol (Life technologies No.11360039), 1 mM Sodium Pyruvate (Life technologies No.11360039), 1×MEM non essential amino acids (10× stock, Life technologies No.11140035), 100 IU/ml penicillin—100 $\mu$g/ml streptomycin (Life technologies No.15140114).
Cytokine Detection Spleen or popliteal lymph node cells were aseptically removed and 1000 $\mu$l of cells in RPMI medium (5% heat-inactivated fetal calf serum, FCS) containing 5×10$^6$ ml of cells were cultured in 24 well flat bottomed plates in the presence of RTS,S or TRAP antigens. The plates were then incubated (37° C., 5% CO$_2$) for a number of hours with 0.5, and 2.5 $\mu$g of antigen, or 4 $\mu$g/ml final of ConA.

The length of time that the cells were incubated depended on the particular cytokine to be detected, IL-2 was stimulated for 72 hours, IL-5 was 72 or 96 hours, and IFN-$\gamma$ was 96 hours. Each cytokine was detected using commercially available ELISA kits (IL-2 and IFN-$\gamma$, Duoset Genzyme No.80-3573-00 and 80-3931-00 respectively; IL-5 was detected using the Pharmingen kit).
Serology Antibodies directed against TRAP were analysed using a sandwich ELISA. A sheep anti-TRAP antiserum was coated onto ELISA plates which was used to capture TRAP antigen added at 0.5 $\mu$g/ml. Titrations of pooled serum from the experimental groups were added and incubated. Finally, biotinylated anti-mouse isotype-specific antibodies followed by streptavidin-peroxidase, were used to detect bound TRAP-specific antibodies.

Anti HBV humoral responses were analysed by a direct ELISA, HBsAg was coated onto the ELISA plate at 1 $\mu$g/ml. Pooled serum from the different experimental groups were titrated and bound antibodies were detected as described above.

Results
Proliferation of Lymphoid Cells in Response to Antigen

The proliferative responses in response to antigen can be seen in the following figures. All vaccine preparations stimulated cells in the local popliteal lymph node which were capable of proliferating in vitro in response to antigen, the magnitude of which was independent of the addition of cholesterol.

All vaccine preparations were capable of stimulating splenic cells which proliferated in vitro in response to antigen. When considering the stimulation indices, the preparations which elicited the highest responses in the spleen were the ones containing cholesterol and those having the low ratio squalene:QS21 (1/5th dose SB62).

Figure 1:
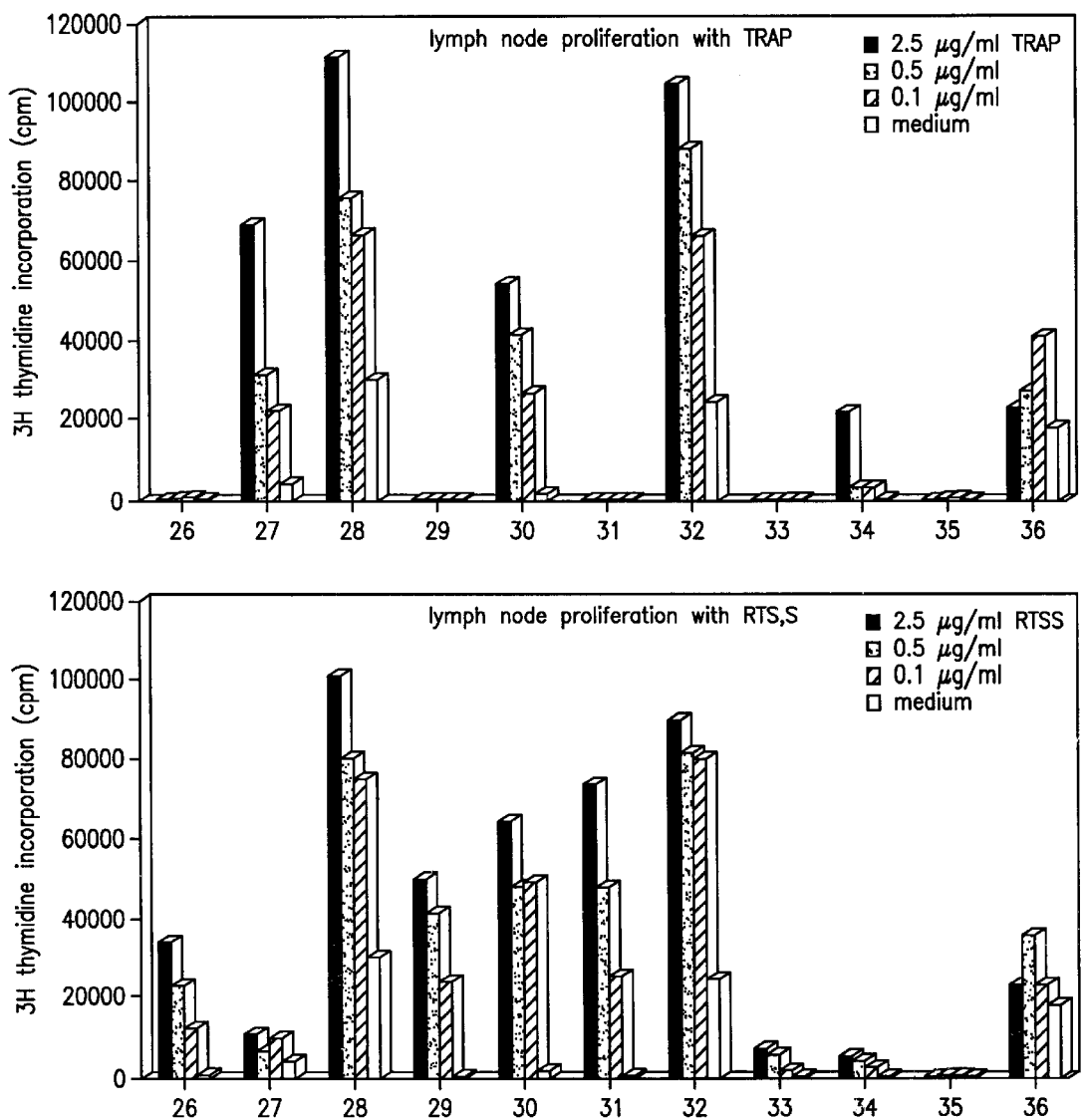
FIG. 1 shows the proliferative responses of popliteal lymph node cells (in raw counts per minute (CPM) form)

FIG. 1, shows the proliferative responses of popliteal lymph node cells (in raw counts per minute (CPM) form) derived from the experimental groups after stimulation with TRAP and RTS,S antigens.

FIG. 2, shows the proliferative responses of splenic cells (in raw counts per minute (CPM) form) derived from the experimental groups after stimulation with TRAP and RTS,S antigens.

FIG. 3, shows the proliferative responses of popliteal lymph node cells (Stimulation index) derived from the experimental groups after stimulation with TRAP and RTS,S antigens.

FIG. 4, shows the proliferative responses of splenic cells (Stimulation index) derived from the experimental groups after stimulation with TRAP and RTS,S antigens.
Discussion of Proliferation Results FIGS. 1 and 2, clearly show that all of the vaccine formulations stimulate lymphoid cells which are capable of proliferating in vitro in the presence of antigen in a dose dependent manner. The raw cpm data suggests that the inclusion of cholesterol in the adjuvant formulations has no effect on the magnitude of the proliferative responses (for example a comparison between groups 26 and 31, termed RTS,S/MPL/QS21/SB62 and RTS,S/MPL/QS21/SB62c respectively).

Examination of the cpm together with the stimulation index results (FIGS. 3 and 4, obtained by dividing the raw cpm for antigen specific proliferation by that derived from non-antigen specific proliferation (medium alone)) shows that the vaccine formulation which generates the highest proliferative responses depends on the origin of the lymphocyte measured. The adjuvant formulations containing the low ratio of squalene:QS21 generate the highest proliferative responses in the spleen. Whereas in the local lymph node whole dose SB62 formulations, with or without cholesterol, generate the highest proliferation responses.

In Vitro Cytokine Production upon Stimulation with Antigen

Cytokine production, measured in vitro in response to antigen, can be both a quantitative and qualitative measure of the induction of immune responses in vivo. In general high levels of IFN-γ and IL-2 are taken to be a measure of Th1-type immune responses and IL-5 is considered to be a Th2-type cytokine. The following figures demonstrate evidence that the addition of cholesterol has no qualitative or quantitative effects on the cytokine profile produced in vitro in response to antigen. The use of SB62' containing a reduced ratio of squalene:QS21 (termed SB62 1/5th dose) had a marked effect in enhancing the production of IFN-γ (FIG. 6).

FIG. 5, shows the IL-2 production of spleen cells after stimulation with TRAP or RTS,S antigen 14 days after VII.

FIG. 6, shows the IFN-γ production by spleen cells after stimulation with TRAP or RTS,S antigen 14 days after VII.

FIG. 7, shows the IL-5 production by spleen cells after stimulation with TRAP or RTS,S antigen 14 days after VII.

Serology

Another measure of immunity that can correlate to a Th1-type, or alternatively a Th2-type, immune response is the IgG sub-isotype which is elicited. A preferential stimulation of the IgGI sub-isotype is generally taken to be a measure of the induction of a $Th^2$-type immune response, and conversely IgG2a and IgG2b is taken to be a measure of a Th1 type immune response.

ELISA studies were performed on pooled mouse serum and the mid-point titres for both the HBsAg and TRAP specific antibodies were ascertained. From these figures, the ratio of the antigen specific IgG1 and IgG2a mid-point titres was calculated and taken to be a measure of the Th1/Th2 balance of the humoral immune response.

TABLE 12

The ratio of IgG1:IgG2a, representing the Th1/Th2 balance. A ratio <1 represents a ThI-type immune response, a ratio of >1 indicating a Th2-type response. Ratio of mid-point titres IgG1:IgG2a

| Group | HBsAg | TRAP |
|---|---|---|
| 26 | 0.44 | |
| 27 | | 0.36 |
| 28 | 1.46 | 1.68 |
| 29 | 0.37 | |
| 30 | 0.39 | 11.83 |
| 31 | 0.28 | |

TABLE 12-continued

The ratio of IgG1:IgG2a, representing the Th1/Th2 balance. A ratio <1 represents a ThI-type immune response, a ratio of >1 indicating a Th2-type response. Ratio of mid-point titres IgG1:IgG2a

| Group | HBsAg | TRAP |
|---|---|---|
| 32 | 0.2 | 7.21 |
| 33 | 0.66 | |
| 34 | 0.3 | 0.77 |

Discussion of Serological Results

Pools of mouse serum were analysed from each group and were found to have successfully stimulated HBsAg and TRAP specific antibodies. In general, antibody mid-point titres against HBsAg were higher than those found against TRAP. The isotype distribution differed between the two antigens. RTS,S in all formulations elicited a clear Th1 pattern, as indicated by an IgG1:IgG2a ratio below 1.

In contrast, TRAP-specific antibodies exhibited a Th2-type isotype pattern. The only exceptions to this observation were groups 2, who received TRAP alone, and group 9, who received TRAP/RTS,S in a SB62' formulation (containing a low ratio of squalene:QS21, termed SB621/5th dose).

EXAMPLE 7

Immunogenicity Studies with Recombinant Antigen S,L*

A study was conducted in Balb/C mice in order to compare the immunogenicity of various S,L* containing formulations. S,L* is a composite antigen comprising a modified surface antigen L protein (L*) and an S-protein both derived from the Hepatitis B virus (HB. This composite antigen is the subject of European Patent application No. EP 0 414 374.

Various formulations with differing ratios of squalene:QS21, optionally with cholesterol at a QS21:cholesterol ratio of 1:10, were combined with S,L* and compared in their ability to induce humoral and cell mediated immune responses (cytokine production and CTL). These oil in water adjuvant emulsions were produced using methods described in example 1. S,L* formulated on Aluminium hydroxide ($AlOH_3$) was used as a Th2 inducing control.

Briefly, groups of 10 mice were immunised intramuscularly 4 times at 3 weeks interval with 2 μg lyophilised S,L* combined with various oil in water emulsion systems (SB62). 14 days following the fourth immunisation the production of cytokines (IL5 and IFN-γ) and CTL activity was analysed after in vitro restimulation of spleen and lymph nodes cells with S,L* antigen. Antibody response to S,L* and the isotypic profile induced were monitored by ELISA at 21 days post II and 14 days post IV.

Groups of Mice

Groups of 10 Balb/C mice were immunised intramuscularly with formulations described below. SB62 was formulated together with the antigen at a normal (240:1, SB62) or low 48:1, SB62') ratio of squalene:QS21, optionally with the addition of cholesterol (c).

TABLE 13

Groups of mice described in example 7:

| Group | Antigen S,L* | Adjuvant name | Composition of adjuvant formulation |
|---|---|---|---|
| GR 1 | 2 μg | SB62 | 25 μl SB62/5 μg QS21/5 μg 3D-MPL |
| GR 2 | 2 μg | SB62c | 25 μl SB62c/5 μg QS21/5 μg 3D-MPL |
| GR 3 | 2 μg | SB62' | 5 μl SB62/5 μg QS21/5 μg 3D-MPL |

TABLE 13-continued

Groups of mice described in example 7:

| Group | Antigen S,L* | Adjuvant name | Composition of adjuvant formulation |
|---|---|---|---|
| GR 4 | 2 μg | SB62'c | 5 μl SB62c/5 μg QS21/5 μg 3D-MPL |
| GR 5 | 2 μg | Alum | 50 μg AlOH$_3$ |

Immunisation Scheme:

Animals were immunised intramuscularly in the leg (50 μl for all groups except for group 5 where 100 μl was injected) at days 0, 21, 42 and 63. Blood was taken from the retroorbital sinus at various time points post immunisations. On day 77, animals from each group were sacrificed, spleens and lymph nodes draining the site of injection (iliac lymph nodes) were taken out for in vitro restimulation. Pools of 3 or 4 spleens and 1 pool of 10 LN were obtained for each group and treated separately in the in vitro assays.

Mouse Serology

Quantitation of anti-HBs antibody was performed by Elisa using HB surface antigen as coating antigen. Antigen and antibody solutions were used at 50 μl per well. Antigen was diluted at a final concentration of 1 μ/ml in PBS and was adsorbed overnight at 4° C. to the wells of 96 wells microtiter plates (Maxisorb Immuno-plate, Nunc, Denmark). The plates were then incubated for 1 hr at 37° C. with PBS containing 1% bovine serum albumin and 0.1% Tween 20 (saturation buffer). Two-fold dilutions of sera (starting at 1/100 dilution) in the saturation buffer were added to the HBs-coated plates and incubated for 1 hr 30 min at 37° C. The plates were washed four times with PBS 0.1% Tween 20 and biotin-conjugated anti-mouse IgG1, IgG2a, IgG2b or Ig (Amersharn, UK) diluted 1/1000 in saturation buffer was added to each well and incubated for 1 hr 30 min at 37° C. After a washing step, streptavidin-biotinylated peroxydase complex (Amersham, UK) diluted 1/5000 in saturation buffer was added for an additional 30 min at 37° C. Plates were washed as above and incubated for 20 min with a solution of o-phenylenediamine (Sigma) 0.04% $H_2O_2$ 0.03% in 0.1% TWEEN 20, 0.05M citrate buffer pH4.5. The reaction was stopped with $H_2SO_4$ 2N and read at 492/620 nm. ELISA titers were calculated from a reference by SoftmaxPro (using a four parameters equation) and expressed in EU/ml.

T Cell Proliferation 2 weeks after the second immunisation, mice were killed, spleen and lymph nodes were removed aseptically in pools (3 or 4 organs per pool for splenic cells, 1 pool of 10 organs for LNC). Cell suspensions were prepared in RPMI 1640 medium (GIBCO) containing 2 mM L-glutamine, antibiotics, 5×10$^{-5}$ M 2-mercaptoethanol, and 1% syngeneic normal mouse serum. Cells were cultured at a final concentration of 2×10$^6$ cells/ml (for LNC or SPC) in 200 μl in round-bottomed 96 well-plates with different concentrations (10–0.03 μg/ml) of S,L* antigen (25D84). Each test was carried out in quadriplicate. After 96 hr of culture at 37° C. under 5% $CO_2$, the cells were pulsed for 18 hr with 3H-Thymidine (Amersham, UK, 5Ci/mmol) at 0.5 μCi/well and then harvested on fibre glass filters with a cell harvester. Incorporated radioactivity was measured in a liquid scintillation counter. Results are expressed in cpm (mean cpm in quadriplicate wells) or as stimulation indices (mean cpm in cultures of cells with antigen/mean cpm in cultures of cells without antigen).

Cytokine Production 2 weeks after the second immunisation, mice were killed, spleen and lymph nodes were removed aseptically in pools (3 or 4 organs per pool for splenic cells, 1 pool of 10 organs for LNC). Cell suspensions were prepared in RPMI 1640 medium (GIBCO) containing 2 mM L-glutarnine, antibiotics, 5×10$^{-5}$ M 2-mercaptoethanol, and 5% foetal calf serum. Cells were cultured at a final concentration of 2.5 to 5×10$^6$ cells/ml (respectively for LNC or SPC) in 1ml, in flat-bottomed 24 well- with different concentrations (1–0.01 μg/ml) of S,L* (25D84). Supernatants were harvested 96 hrs later and frozen until tested for the presence of IFNg and IL-5 by Elisa.

IFN-γ Production

Quantitation of IFNγ was performed by Elisa using reagents from Genzyme. Samples and antibody solutions were used at 50 μl per well. 96-well microtiter plates (Maxisorb Immuno-plate, Nunc, Denmark) were coated overnight at 4°C. with 50 μl of hamster anti-mouse IFNg5 diluted at 1 μg/ml in carbonate buffer pH 9.5. Plates were then incubated for 1 hr at 37° C. with 100 μl of PBS containing 1% bovine serum albumin and 0.1% Tween 20 (saturation buffer). Two-fold dilutions of supernatant from in vitro stimulation (starting at 1/2) in saturation buffer were added to the anti-IFNg5-coated plates and incubated for 1 hr 30 at 37° C. The plates were washed 4 times with PBS Tween 0.1% (wash buffer) and biotin-conjugated goat anti-mouse IFNg diluted in saturation buffer at a final concentration of 0.5 μg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 μl of TMB (Biorad) for 10 min. The reaction was stopped with $H_2SO_4$ 0.4N and read at 450 nm. Concentrations were calculated using a standard curve (mouse IFNγ standard) by SoftmaxPro (four parameters equation) and expressed in pg/ml.

IL-5 Production

Quantitation of IL5 was performed by Elisa using reagents from Pharmingen. Samples and antibody solutions were used at 50 μl per well. 96-well microtiter plates (Maxisorb Immuno-plate, Nunc, Denmark) were coated overnight at 4° C. with 50μl of rat anti-mouse IL5 diluted at 1 μg/ml in carbonate buffer pH 9.5. Plates were then incubated for 1 hr at 37° C. with 100 μl PBS containing 1% bovine serum albumin and 0.1% TWEEN 20 (saturation buffer). Two-fold dilutions of supernatant from in vitro stimulation (starting at 1/2) in saturation buffer were added to the anti-IL5-coated plates and incubated for 1 hr 30 at 37° C. The plates were washed 4 times with PBS Tween 0.1% (wash buffer) and biotin-conjugated rat anti-mouse IL5 diluted in saturation buffer at a final concentration of 1 μg/ml was added to each well and incubated for 1 hr at 37° C. After a washing step, AMDEX conjugate (Amersham) diluted 1/10000 in saturation buffer was added for 30 min at 37° C. Plates were washed as above and incubated with 50 μl of TMB (Biorad) for 15 min. The reaction was stopped with $H_2SO_4$ 0.4N and read at 450 nm. Concentrations were calculated using a standard curve (recombinant mouse IL5) by SoftmaxPro (four parameters equation) and expressed in pg/ml.

CTL Induction 2 weeks after the second immunisation, mice were killed, spleens were removed aseptically in pools of 3 or 4 mice (2 pools of 3 and one pool of 4 mice per group). Cell suspensions were prepared in RPMI 1640 medium (GIBCO) containing 2 mM L-glutamine, antibiotics, 5×10$^6$ M 2-mercaptoethanol, and 5% foetal calf serum. Cells were cultured at a final concentration of 2×10$^6$ cells/ml in 10 ml medium containing 2 μg/ml S,L* and 1.25% ConA sup (25 cm$^2$ Falcon flasks) and incubated for 8 days at 37° C. under 5% $CO_2$.

CTL Assay

The day before the CTL assay (d7), target cells were prepared by incubation of P815 cells ($10^6$ cells/ml) with S,L* or peptide $S_{28-39}$ at 10 μg/ml. Following 1 hr incubation in 15 ml Falcon tubes in a small volume, cells are transferred to 24 well plates and incubated ON at 37° C.

The day of the assay, $2 \times 10^6$ S,L* and $S_{28-39}$ pulsed P815 cells and P815-S are centrifugated, resuspended in 50 μl FCS and incubated with 75 μl $^{51}$Cr (375 μCi) for 1 hr at 37° C. (shaking every 15'). Cells are then washed 4 times with 10 ml complete medium and incubated for 30' at 4° C. following the 4th wash. Cells are then centrifugated and resuspended at a concentration of $2 \times 10^4$ cells/ml.

Effector cells are then centrifugated, counted and resuspended at $2 \times 10^6$ cells/ml. Three fold serial dilutions of effector cells are done in 96 V-bottomed plates, starting at a concentration of $2 \times 10^5$ cells /well/100 μl.

$2 \times 10^3$ target cells in 100 μl are added to effector cells in triplicate. Spontaneous and maximum release are assessed by incubating target cells respectively with medium or Triton X100 3%.

Plates are centrifugated 3' at 700 rpm and incubated for 4 hrs at 37° C. Following the incubation time, 50 μl of supernatant is transfered from each well to Luma-plates and dryed overnight before counting in Top-count scintillation counter.

Results are expressed as specific lysis and calculated as follows:

% SR=(mean cpm sample−mean cpm medium/mean cpm max−mean cpm medium)×100

Results

Serology

Humoral responses (Ig and isotypes) were measured by Elisa using HB surface antigen as coating antigen. Only the time point: 21 days post II was analysed. The results are shown in FIG. 8 and 9.

FIG. 8, Shows the titres of anti-Hepatitis B virus antibody responses (Ig) expressed as both individual mouse sera and average (21 days post II).

FIG. 9, Shows the sub-isotype distribution of Hbs specific IgG in the serum the vaccinated mice.

As can be seen in FIG. 8, SB62 related formulations induce much higher antibody titers than the S,L* Alum formulation.

Analysis of mean titres from individual sera suggest that higher antibody titers are obtained with SB62c and SB62'c formulations (roughly 2 fold higher antibody titers than SB62 and SB62' respectively).

Statistical analysis on individual sera (Anoval test Newman Keuls) show no significant difference in antibody titers induced by SB62c and SB62'c or equally between the antibody titers induced by SB62 and SB62'c.

The sub-isotypic distribution profile (as shown in FIG. 9) is comparable for all SB62 related formulations (25–30% IgG2a) whereas Alum induce only 4% IgG2a.

Cell-mediated Immune Responses

Cell-mediated immune responses (lymphoproliferation, IFNγ/IL5 production and CTL) were measured at 14 days post IV after in vitro restimulation of splenic and iliac lymph nodes cells with S,L* antigen.

Cytokine Production

Cytokine production (IFN-γ and IL-5) has been measured following 96 h of in vitro restimulation of splenic cells and iliac lymph node cells with S,L*. The results are shown in FIGS. 10 to 13.

FIG. 10, Shows the results of analysis of IFN-γ production by splenic cells (mean of data obtained with three pools/group).

FIG. 11, Shows the results of analysis of IL-5 production by splenic cells (mean of data obtained with three pools/group).

FIG. 12, Shows the results of analysis of IFN-γ production by Iliac lymph node cells (mean of data obtained with three pools/group).

FIG. 13, Shows the results of analysis of IL-5 production by Iliac lymph node cells (mean of data obtained with three pools/group).

TABLE 14

Ratio of IFN-γ: IL-5 producing cells detected in splenic cells

| Restimulation | Groups | | | | |
| --- | --- | --- | --- | --- | --- |
| | GR1 | GR2 | GR3 | GR4 | GR5 |
| S,L* 10 μg/ml | 22.9 | 10.7 | 51.7 | 17.0 | 0.9 |

Discussion

A IFN-γ:IL-5 ratio >1 clearly suggests that a pro TH1 response is induced by SB62 related formulations (calculated at 10 μg/ml S,L*) (see table 14).

The strongest IFN-γ production is obtained after restimulation of splenic cells from animals immunised with S,L* SB62' and SB62'c. SB62c formulations induce stronger IFN-γ production than the corresponding SB62 formulations (splenic cells).

Higher levels of IL-5 are produced by animals immunised with S,L* SB62c formulations than S,L* SB62 formulations not containing cholesterol. S,L* Alum immunised animals produce the highest levels of IL-5.

No significant difference is observed in ileac lymph node cell IFN-γ production between SB62 and SB62c formulations.

The strongest IFN-γ production is obtained after restimulation of splenic cells from animals immunised with S,L* SB62'c.

Cytotoxic T Cell Responses

S,L* specific CTL responses observed in the spleen cells of mice two weeks after the second immunisation are shown in FIG. 14.

FIG. 14, Shows the CTL activity of splenic T-cells stimulated in vitro for 7 days with S,L* antigen (mean % specific lysis of three pools).

Discussion

S,L* specific CTL is stimulated by vaccination with all oil in water emulsion formulations.

A stronger CTL response is observed with formulations containing SB62' emulsions when looking at limiting E/T ratio such as 3/1.

Conclusions

1. The TH1 type profile of the immune response induced by all SB62 related formulations is further confirmed by the IFN-γ/IL-5 ratio.
2. A comparable isotypic profile (25–30% IgG2a) is obtained with all SB62 related formulations suggesting the induction of a TH1 type HBs specific immune response.

3. All SB62 related formulations induce specific CTL, with a slight improvement seen by administration of SB62'.
4. No significant difference is observed between antibody titers induced following immunisation with SB62c and SB62'.
5. The strongest IFN-Y production is observed following immunisation with SB62'c.

TABLE 15

Summary table of the immune parameters induced by the vaccine formulation described in example 7.

| Immune parameter | Formulations containing S,L * | | | | |
|---|---|---|---|---|---|
| | SB62 | SB 62c | SB62' | SB62'c | Alum |
| Ab titers | +++ | +++ | ++ | +++ | + |
| TH type (% IgG2a) | TH1 (29) | TH1 (26) | TH1 (29) | TH1 (30) | TH2 (4) |
| IFN-γ | + | ++ | +++ | ++++ | + |
| IL-5 | − | + | + | ++ | +++ |
| CTL | + | + | ++ | ++ | − |

EXAMPLE 8

Reactogenicity Study in Rabbits Using L2E7 Antigen Formulated in Various SB62 Adjuvants This study investigated the reactogenicity of various vaccine formulations after administration into rabbits. Formulations were given intramuscularly (IM, in a 500 μl volume) as a single administration on day 0, in male white New Zealand rabbits weighing between 2 and 2.5 kg (5 animals in each group). Blood was collected on day −5, +1, +2, +3 and +4 for PMN and CPK determinations. Additional bleedings were performed on day −7 and in order to get the PMN background of the animals prior injection. On day 4, animals were sacrificed and necropsied in order to examine the injection site macroscopically. The injection site was collected and preserved in formaldehyde for histopathological examinations.

The antigen used in this study is a fusion protein comprising the L2 and E7 proteins from Human Papilloma virus. L2E7 fusion proteins are disclosed in GB 95/15478.7.

CPK (creatin phosphate kinase) is a marker of muscle lesion and can be used as a read-out to assess the local reactogenicity during muscle damage. PMN (polymorphonuclear neutrophils) is used to assess both local and inflammatory process induced by the injection and, in a lesser extent, systemic side-effects related to this local inflammation (flu-like symptoms, fever, headache).

TABLE 16

Groups of animals used in example 8

| Group | Antigen | Diluant |
|---|---|---|
| A | L2E7 (300 μg) | SB62 |
| B | L2E7 (300 μg) | SB62c |
| C | L2E7 (300 μg) | PBS pH 6.8 |
| D | — | SB62 |
| E | — | SB62c |
| F | — | PBS pH 6.8 |

Results

PMN

During the course of the experiment (excluding day 1 post vaccination), all rabbits at had an average baseline of PMNs at 25.7% of total cells (SD 7.6).

In the control group that received PBS alone, the level of PMNs remained at baseline throughout the course of the experiment, that is 24.2% from day −7 to day +4, (SD 5.8). The results can be summarized as follows:

| Group | % PMNs average before and after injection (days −7, −5, +3 and +4) | % PMNs average after injection day 1 | % PMNs difference | % of ncrease |
|---|---|---|---|---|
| A | 22.1% (+/−5.6%) | 50.6% (+/−5.3%) | 27.8% | 122% |
| B | 24.1% (+/−7.2%) | 56% (+/−6.9%) | 31.9% | 132% |
| C | 24.9% (+/−7.6%) | 35.2% (+/−8.7%) | 10.3% | 41% |
| D | 23.5% (+/−5.2%) | 56.7% (+/−9.3%) | 33.2% | 141% |
| E | 25.1% (+/−6.4%) | 59.3% (+/−7.1%) | 34.2% | 136% |
| F | 23.1% (+/−6.1%) | 27.4% (+/−5.8%) | 4.3% | 19% |

Discussion

Injection of SB62 or SB62c alone or in combination with antigen induced strong responses in PMN levels on day 1 post vaccination. The addition of cholesterol therefore had no effect on inflammatory responses post vaccination.

Injection of L2E7 in PBS induces an only slight increase in PMNs percentage (41% increase) despite the high concentration of antigen used (300 μg).

No significant difference in PMNs percentage is observed in the control group during the whole experiment.

CPK

Individual CPK(U/L) results measured on day −5, 1, 2, 3 and 4 are shown in FIG. 15. The results can be summarised as follows:

SB62 formulations with or without antigen induce a significant increase in CPK on day 1.

SB62c formulations with or without antigen do not induce significant CPK release on day 1.

FIG. 15, Summary figure shows the mean CPK results for each group.

Histopathological Analyses

Individual data from histopathological analyses are shown in Table 17, and can be summarized as follows:

Macroscopical examinations at necropsy on day 4 revealed abnormalities at the site of injection in animals that had received SB62 based formulations with or without antigen. Most animals treated with SB62 based formulations with or without antigen showed a wide local muscle lesion.

Local muscle damage was significantly reduced when SB62c was used (small spots in all rabbits except for 2 animals that developed lesions that are smaller than lesions induced by SB62).

No abnormalities were detected in PBS or antigen vaccinated animals (besides slight lymphocyte infiltrate in 2 animals treated with antigen and 1 animal treated with PBS).

Microscopic examinations showed some histological changes at the injection site related to muscle damage (necrosis, rhabdomyolysis, haemorrhage) and local inflammatory process (lymphocyte and monocyte infiltrates). These signs were observed in all rabbits injected with SB62 based formulations with or without antigen, and were much more severe than those observed in animals injected with SB62c containing formulations.

Histological examination of the site of injection confirms the CPK release data showing a significant reduction in local damage with SB62c formulations.

TABLE 17

Histological examination result with SB62 based formulations with L2E7 antigen.

| Group | Rabbit | Site of injection les | size (mm) | necro | rhabdo | infiltr | haemo | infl apone | Remark |
|---|---|---|---|---|---|---|---|---|---|
| A | 4 | + | 30x15x5 | 3 | 2 | 3 | 2 | 2 | |
|   | 15 | + | 24x7x4 | 3 | 2 | 2 | 2 | 2 | |
|   | 17 | + | 25x10x3 | 3 | 2 | 2 | 2 | 2 | |
|   | 27 | + | 27x14x8 | 3 | 2 | 3 | 2 | 2 | |
|   | 28 | + | 25x8x5 | 3 | 2 | 3 | 3 | 2 | |
| B | 2 | + | 10x2x1 | 1 | 2 | 2 | 1 | 1 | |
|   | 11 | s | 0 | 0 | 0 | 0 | 0 | 1 | |
|   | 21 | + | 15x8x2 | 0 | 0 | 2 | 1 | 2 | infl diffus |
|   | 22 | – | 0 | 0 | 0 | 1 | 0 | 2 | infl diffus |
|   | 29 | s | 0 | 0 | 2 | 2 | 1 | 2 | |
| C | 1 | s | s | 0 | 0 | – | 0 | 0 | |
|   | 3 | – | – | 0 | 0 | – | 0 | 1 | |
|   | 18 | – | – | 0 | 0 | – | 0 | 1 | |
|   | 23 | – | – | 0 | 0 | 1 | 0 | 1 | |
|   | 24 | – | – | 0 | 0 | 2 | 0 | 1 | |
| D | 5 | + | 10x3x2 | 2 | 2 | 3 | 1 | 1 | |
|   | 7 | s | s | 0 | 0 | 0 | 0 | 1 | |
|   | 9 | + | 18x10x4 | 3 | 3 | 3 | 1 | 2 | |
|   | 14 | + | 16x2x5 | 3 | 3 | 3 | 1 | 2 | |
|   | 33 | s | s | 0 | 1 | 2 | 0 | 2 | |
| E | 8 | s | s | 0 | 1 | 2 | 1 | 2 | |
|   | 10 | s | s | 0 | 1 | 2 | 0 | 2 | |
|   | 20 | s | s | 0 | 1 | 2 | 0 | 2 | |
|   | 25 | s | s | 1 | 1 | 1 | 0 | 2 | infl diffus |
|   | 30 | s | s | 0 | 1 | 1 | 0 | 2 | |
| F | 6 | – | – | 0 | 0 | 2 | 0 | 2 | |
|   | 13 | – | – | 0 | 0 | 0 | 0 | 0 | |
|   | 16 | – | – | 0 | 0 | 0 | 0 | 0 | |
|   | 26 | – | – | 0 | 1 | 2 | 0 | 0 | |
|   | 34 | – | – | 0 | 0 | 0 | 0 | 0 | | footnotes:
les = lesion
necro = necrosis
infiltr = lymphocytic infiltration
inf apone = lymphocytic infiltration in muscle aponevrose
haemo = haemorrhage
rhabdo = rhabdomyolosis
infl diffus = infiltration diffuse
Gradation:
0 = no sign
1 = very slight
2 = slight
3 = moderate
4 = severe
+ = present
s = spot
– = no sign

EXAMPLE 9

Stabilisation of QS21 by Addition of Cholesterol

It has previously been described that QS21-H is hydrolysis product of QS21. that is no longer active as adjuvant. It is formed by cleavage of the QS21 molecule by OH$^-$ from the aqueous solution. This reaction occurs where the pH of the aqueous medium is above a value of 6.5, and is accelerated by higher temperature. The oil-in-water emulsions described in this patent application (for example SB62) are known to exhibit a stabilising effect such that the hydrolysis of QS21 into QS21-H is inhibited. Upon dilution of the oil in water emulsion in the presence of constant QS21, they lose this stabilising property and the QS21 degenerates into the inactive QS21-H form. Surprisingly, emulsions containing additional Cholesterol, who at 1/1 ratio do not show an improved QS21 stability, maintain the stabilising effect even at a 1/5 dilution.

QS21 and QS2-H are assayed directly into the emulsion. This is achieved by chemically derivatising the complete formulation, and by performing a selective extraction step that dissolves the QS21, but leaves most interfering matrix compounds behind. The assay is HPLC based, and the compounds are dansylated. The dansylation is performed by drying down a sample of the emulsion, and adding 100 $\mu$l of 3.5 mg Dansyl hydrazine/ml C/M 2/1 and 100 $\mu$l of 1:4 Acetic acid: C/M 2/1 in that order. The mixture is well vortexed and incubated at 60° C. for 2 hours. The reaction mixture is dried in the Speedvac. It is reconstituted in 500 $\mu$l 30% ACN in H2O, and centrifugated twice at 14000 rpm for two minutes. The supernatants are then collected in an autosampler tube. A standard curve is obtained by preparing QS21 and QS21-H in a mixture that contains the same compounds as the emulsion under study.

The HPLC assay is ran on a Vydac 218TP54 5 $\mu$ particle size C18 RP column, 250*4.6 mm. Solvents are A:H20+0, 05% TFA(trifluoracetic acid) and B:Acetonitrile +0,05% TFA. The gradient table is:

| Time (min) | % A | % B |
|---|---|---|
| 0 | 70 | 30 |
| 2 | 70 | 30 |
| 15 | 50 | 50 |
| 17 | 50 | 50 |
| 17.1 | 10 | 90 |
| 19 | 10 | 90 |
| 21 | 70 | 30 |
| 25 | 70 | 30 |

The flow rate is 1 ml/min. Detection is in fluorescence, with excitation at 345 nm and emmision at 515 nm. 50 $\mu$l is injected of both the sample and the standards. The column heater is set to 37° C. for this separation. Peaks for QS21, QS21-iso and QS21-H are distinguishedon the chromatogram.

A series of samples with the following composition were analysed:

| Composition | SB62 | SB62c | MPL | QS21 |
|---|---|---|---|---|
| SB62 | 250 $\mu$l | — | 50 $\mu$g | 50 $\mu$g |
| SB62' | 50 $\mu$l | — | 50 $\mu$g | 50 $\mu$g |
| SB62c | — | 250 $\mu$l | 50 $\mu$g | 50 $\mu$g |
| SB62'c | — | 50 $\mu$l | 50 $\mu$g | 50 $\mu$g |

Assay of QS21/QS21-H was performed after incubation of the samples at various time intervals and tempetures (4° C. and 37° C.). The data for 1 month at 37° C. in this model correlate well with stability of QS21 after prolonged storage at 4° C. (eg 2 years).

Table 18, HPLC QS21 assay: % of QS21-H generated over time

| Composition | 3 months (4° C.) | 6 months (4° C.) | 3 months (4° C.) + 7 days (37° C.) | 1 month (37° C.) |
|---|---|---|---|---|
| SB62 | 1% | 2% | 3% | 15% |
| SB62' | 1% | 1% | 9% | 31% |
| SB62c | 2% | 2% | 3% | 17% |
| SB62'c | 2% | 2% | 3% | 21% |

This results shown in the table above shows clearly (both for 7days and 1 m) the effect of adding a sterol, in this case cholesterol, to SB62' in maintaining the stability of QS21.

SUMMARY OF THE INVENTION

It is clear from the examples above that the present invention encompasses an oil in water emulsion which preferentially induces a strong Th1-type immune responses. Embodiments of the present invention, as described in the examples, include composition comprising an oil in water emulsion, a saponin and a sterol, characterised in that a reduced reatogenicity profile is induced upon administration to a host in comparison to the reactogenicity profile observed after administration of the same composition from which the sterol has been omitted. The addition of cholesterol, however, does not adversly affect quantitatively or qualitatively the immune responses thus induced.

What is claimed is:

1. A composition comprising an oil in water emulsion having an oil phase and an aqueous phase and a saponin, wherein the oil phase of said oil in water emulsion comprises a metabolizable oil and a sterol and the saponin is in the aqueous phase.

2. A composition as claimed in claim 1, where the sterol is cholesterol.

3. A composition as claimed in claim 1, wherein said metabolizable oil is squalene.

4. A composition as claimed in claim 1, wherein said saponin is a derivate of QuliA.

5. A composition as claimed in claim 4, wherein said QuilA derivative is selected from the group consisting of QS21 and QS17.

6. A composition as claimed in claim 1, further containing one or more other immunomodulators.

7. A composition as claimed in claim 6, wherein the immunomodulators are selected from the group consisting of 3D-MPL and α-tocopherol.

8. A composition for raising an immune response comprising a composition as claimed in any one of claims 1 to 7, further comprising an antigen or antigenic preparation.

9. A composition for raising an immune response as claimed in claim 8, where the antigen or antigenic preparation is prepared from the group comprising: Human Immunodeficiency Virus; Herpes Simplex Virus type 1; Herpes Simplex Virus type 2, Human Cytomegalovirus; Hepatitis A, B, C or E; Respiratory Syncytial Virus, Human Papilloma Virus; Influenza Virus, Salmonella; Neisseria,; Borrelia; Chlamydia; Bordetella; Plasmodium, Toxoplasma, tuberculosis and EBV.

10. A composition for raising an immune response as claimed in claim 8, wherein the antigen or antigenic preparation is a combination of the Malaria antigens RTS, S and TRAP.

11. A composition for raising an immune response as claimed in claim 8, wherein the antigen or antigenic preparation is, or is derived from, a tumor or host derived antigen.

12. A method for manufacturing a composition as claimed in claim 8 comprising admixing (a) an oil in water emulsion wherein the oil droplets comprise a sterol; (b) an aqueous solution of QS21; and (c) an antigen or antigenic preparation.

13. A method for manufacturing a composition as claimed in claim 12 wherein said sterol is cholesterol.

14. A method of treating an individual susceptible to or suffering from a disease by the administration of a vaccine composition as claimed in claim 8.

15. A composition as claimed in claim 1, wherein the oil in water emulsion comprises oil droplets which have a diameter which is less than 1 micron.

16. A composition as claimed in claim 1, wherein the oil in water emulsion comprises oil droplets which are in the range of 120 to 750 nm in diameter.

17. A composition as claimed in claim 1, wherein the oil in water emulsion comprises oil droplets which are in the range of 120 to 600 nm in diameter.

18. A composition as claimed in claim 1, wherein the saponin present in the aqueous phase of the oil in water emulsion is stabilized in its non-hydrolyzed, adjuvant active form.

19. A method as claimed in claim 18, wherein the saponin is QS21.

20. A method as claimed in claims 18 or 19, wherein the sterol is cholesterol.

21. A method as claimed in claim 18, characterised in the oil phase of said oil in water emulsion comprises squalene, said saponin is QS21, and wherein the ratio of squalene:QS21 is substantially 48:1 (w/w).

22. A composition comprising an oil in water emulsion having an oil phase and an aqueous phase, and QS21, the oil phase comprises squalene and cholesterol and said QS21 is in the aqueous phase of said oil in water emulsion, wherein the ratio of QS21:cholesterol is in the range of 1:1 to 1:10 (w/w).

23. A composition as claimed in claim 22, wherein the ratio of squalene:QS21 is in the range from 1:1 to 250:1 (w/w).

24. A composition as claimed in claims 22, wherein the ratio of squalene:QS21 is substantially 48:1 (w/w).

25. A method of treating an individual susceptible to or suffering from a disease by the administration of a composition as claimed in any one of claims 1 to 7.

* * * * *